(12) United States Patent
Ho et al.

(10) Patent No.: US 12,280,155 B2
(45) Date of Patent: Apr. 22, 2025

(54) COMPOSITION FOR INCREASING THE EXPRESSION OF A GROWTH FACTOR GENE, COMPRISING CORESHELL STRUCTURED MICROPARTICLES AS ACTIVE INGREDIENT

(71) Applicants: G&P BIOSCIENCE CO., LTD., Seoul (KR); REYON PHARMACEUTICAL CO., LTD., Seoul (KR)

(72) Inventors: Seong-Hyun Ho, Seoul (KR); Su Jin Park, Gyeonggi-do (KR)

(73) Assignees: G&P BIOSCIENCE CO., LTD., Seoul (KR); REYON PHARMACEUTICAL CO., LTD., Seoul (KR)

( * ) Notice: Subject to any disclaimer, the term of this patent is extended or adjusted under 35 U.S.C. 154(b) by 824 days.

(21) Appl. No.: 16/969,092

(22) PCT Filed: Feb. 12, 2019

(86) PCT No.: PCT/KR2019/001708
§ 371 (c)(1),
(2) Date: Dec. 28, 2020

(87) PCT Pub. No.: WO2019/156540
PCT Pub. Date: Aug. 15, 2019

(65) Prior Publication Data
US 2021/0113668 A1    Apr. 22, 2021

(30) Foreign Application Priority Data
Feb. 12, 2018   (KR) .................. 10-2018-0017075
Feb. 8, 2019    (KR) .................. 10-2019-0014955

(51) Int. Cl.
| | | |
|---|---|---|
| A61K 9/50 | (2006.01) | |
| A61K 31/02 | (2006.01) | |
| A61K 31/025 | (2006.01) | |
| A61K 31/035 | (2006.01) | |
| A61K 33/16 | (2006.01) | |
| A61K 38/18 | (2006.01) | |
| A61K 38/30 | (2006.01) | |
| A61K 38/37 | (2006.01) | |
| A61K 47/06 | (2006.01) | |
| A61K 47/18 | (2017.01) | |
| A61K 47/24 | (2006.01) | |
| A61K 47/26 | (2006.01) | |
| A61K 47/28 | (2006.01) | |

(Continued)

(52) U.S. Cl.
CPC .......... *A61K 9/5015* (2013.01); *A61K 31/02* (2013.01); *A61K 31/025* (2013.01); *A61K 31/035* (2013.01); *A61K 33/16* (2013.01); *A61K 38/1833* (2013.01); *A61K 38/30* (2013.01); *A61K 38/37* (2013.01); *A61K 47/06* (2013.01); *A61K 47/186* (2013.01); *A61K 47/24* (2013.01); *A61K 47/26* (2013.01); *A61K 47/28* (2013.01); *A61P 7/04* (2018.01); *A61P 25/02* (2018.01); *A61K 48/00* (2013.01)

(58) Field of Classification Search
None
See application file for complete search history.

(56) References Cited

U.S. PATENT DOCUMENTS

| | | |
|---|---|---|
| 6,638,767 B2 † | 10/2003 | Unger |
| 7,427,602 B1 | 9/2008 | Shea et al. |

(Continued)

FOREIGN PATENT DOCUMENTS

| | | |
|---|---|---|
| CN | 100551440 | 3/2007 |
| JP | 2001-507207 | 6/2001 |

(Continued)

OTHER PUBLICATIONS

Zhou, Zhiyi, et al. "Synergistic effects of ultrasound-targeted microbubble destruction and TAT peptide on gene transfection: an experimental study in vitro and in vivo." Journal of Controlled Release 170.3 (2013): 437-444. (Year: 2013).*

Unger, Evan C., et al. "Gene delivery using ultrasound contrast agents." Echocardiography 18.4 (2001): 355-361. (Year: 2001).*

Vannan, Mani, et al. "Ultrasound-mediated transfection of canine myocardium by intravenous administration of cationic microbubble-linked plasmid DNA." Journal of the American Society of Echocardiography 15.3 (2002): 214-218. (Year: 2002).*

(Continued)

*Primary Examiner* — Bethany P Barham
*Assistant Examiner* — Peter Anthopolos
(74) *Attorney, Agent, or Firm* — DUANE MORRIS LLP; Gregory M. Lefkowitz; Brandon A. Chan

(57) ABSTRACT

The present disclosure relates to a composition for increasing the expression of a growth factor gene, which contains core-shell structured microparticles as an active ingredient. When administered in vivo along with a growth factor gene, the composition for increasing the expression of a growth factor gene of the present disclosure can increase the expression of the co-administered gene by at least 30%. Especially, when administered along with at least one gene selected from a human hepatocyte growth factor (HGF) gene, an isoform gene of the human hepatocyte growth factor and a variant gene thereof, or at least one gene selected from a human insulin-like growth factor 1 (IGF1) gene, an isoform gene of the human insulin-like growth factor 1 and a variant gene thereof, which are appropriate for the present disclosure, the composition can increase the expression of the gene by at least 30%. When administered along with a gene therapeutic agent, the composition can achieve a therapeutic effect even with a very small amount of a gene, and thus is useful.

5 Claims, 6 Drawing Sheets

Specification includes a Sequence Listing.

(51) Int. Cl.
  *A61K 47/69* (2017.01)
  *A61K 48/00* (2006.01)
  *A61P 1/16* (2006.01)
  *A61P 7/04* (2006.01)
  *A61P 9/10* (2006.01)
  *A61P 13/12* (2006.01)
  *A61P 25/00* (2006.01)
  *A61P 25/02* (2006.01)

(56) References Cited

U.S. PATENT DOCUMENTS

| | | | |
|---|---|---|---|
| 9,750,769 B2 † | 9/2017 | Hazel | |
| 9,963,493 B2 † | 5/2018 | Kim | |
| 2001/0031740 A1 | 10/2001 | Unger | |
| 2003/0018984 A1 | 1/2003 | Coleman | |
| 2005/0059598 A1* | 3/2005 | Clark | A61P 5/48 514/8.6 |
| 2009/0041833 A1 | 2/2009 | Bettinger | |
| 2009/0263359 A1 | 10/2009 | Ferreira et al. | |
| 2013/0022550 A1 | 1/2013 | Unger | |
| 2016/0120942 A1 | 5/2016 | Hazel | |
| 2017/0333527 A1* | 11/2017 | Fukuta | A61K 47/183 |

FOREIGN PATENT DOCUMENTS

| | | | |
|---|---|---|---|
| JP | 2003-095988 | 4/2003 | |
| KR | 1005628240000 | 3/2006 | |
| KR | 1020140063697 | 5/2014 | |
| KR | 1020150032944 | 3/2015 | |
| KR | 1020170075771 | 7/2017 | |
| KR | 1021000210000 | 4/2020 | |
| WO | 9515118 A1 | 6/1995 | |
| WO | WO-2007008220 A2 * | 1/2007 | A61K 41/0028 |
| WO | 2016154288 A1 | 9/2016 | |

OTHER PUBLICATIONS

Unger, Evan C., et al. "Therapeutic applications of lipid-coated microbubbles." Advanced drug delivery reviews 56.9 (2004): 1291-1314. (Year: 2004).*

Yuan, Qiao-Ying, et al. "A visible, targeted high-efficiency gene delivery and transfection strategy." BMC biotechnology 11 (2011): 1-10. (Year: 2011).*

Lee, Sang-Chol, et al., "Enhancement of Gene Delivery in Mouse Skeletal Muscle with Microbubble Destruction by Low-Frequency Ultrasound," Korean Circulation J, 2006, 36:32-38.

Shen, Z.P., et al., "Ultrasound with microbubbles enhances gene expression of plasmid DNA in the liver via intraportal delivery," Gene Therapy, 2008, 15:1147-1155.

Li, X., "Experimental Research on Therapeutic Angiogenesis Induced by Hepatocye Growth Factor Directed by Ultrasound-Targeted Mirobubble Destruction in Rats," J Ultrasound Med, 2008, 27:453-460.

Lee, Y.J., et al., "Improved Expression of Vascular Endothelial Growth Factor by Naked DNA in Mouse Skeletal Muscles: Implication for Gene Therapy of Ischemic Diseases," Biochemical and Biophysical Research Communications, 2000, 272:230-235.

Liu, Y., et al., "Encapsulated ultrasound microbubbles: Therapeutic application in drug/gene delivery," Journal of Controlled Release, 2006, vol. 114, pp. 89-99.

Zhou, Z., et al., "Synergistic effects of ultrasound-targeted microbubble destruction and TAT peptide on gene transfection: An experimental study in vitro and in vivo," Journal of Controlled Release, 2013, vol. 170, pp. 437-444.

Tang, Y., et al., "Use of ultrasound-targeted microbubble destruction to transfect IGF-1 cDNA to enhance the regeneration of rat wounded Achilles tendon in vivo," Gene Therapy, 2015, vol. 22, 610-618.

Jiang, et al., Attenuation of hepatic fibrosis through ultrasound-microbubble-mediated HGF gene 1 transfer in rats, p. 105, Table 2 and Abstract, Clinical Imaging.†

Tang, Use of ultrasound-targeted microbubble destruction to transfect IGF-1 cDNA to enhance 2 the regeneration of rat wounded Achilles tendon, Abstract, 2015, Gene Therapy in vivo.†

SonoVue Product Monograph, pp. 15 and 29, Dec. 20, 2016, Bracco.†

* cited by examiner
† cited by third party

COMPOSITION FOR INCREASING THE EXPRESSION OF A GROWTH FACTOR GENE, COMPRISING CORESHELL STRUCTURED MICROPARTICLES AS ACTIVE INGREDIENT

SEQUENCE LISTING

The instant application contains a Sequence Listing, which has been submitted electronically in ASCII format, and is hereby incorporated by reference in its entirety. Said ASCII copy, created on Oct. 15, 2020, is named G1035-17201_RevisedSequenceList.txt and is 30,621 bytes in size.

TECHNICAL FIELD

The present disclosure relates to a composition for increasing the expression of a growth factor gene, which contains core-shell structured microparticles as an active ingredient.

BACKGROUND ART

Human hepatocyte growth factor (HGF) is secreted from mesoderm-derived cells and exerts various functions depending on target cells and environments (Stella, M. C. and Comoglio, P. M., *The International Journal of Biochemistry & Cell Biology*, 31: 1357-1362 (1999)). Its functions include: 1) induction of tubular structure formation by epithelial cells by facilitating division and motility of the epithelial cells and enhancing their ability of matrix invasion; 2) stimulation of vascularization by endothelial cells both in vitro and in vivo; 3) regeneration of the liver and kidney owing to its anti-apoptosis activity; 4) organogenesis of the kidney, ovary and testis during embryonic development; 5) control of osteogenesis through regulation of the function of osteoclasts and osteoblasts; 6) promotion of the growth and differentiation of erythropoietic progenitor cells; and 7) axon sprouting of neurons. Based on these various functions, the hepatocyte growth factor may be developed as a therapeutic agent for various diseases, e.g., ischemic diseases, neurological diseases, kidney diseases or liver diseases.

Human insulin-like growth factor 1 (IGF1) is a polypeptide hormone consisting of 70 amino acids, which has insulin-like activity and mitogenic activity. This hormone enhances cell growth in various tissues such as the musculoskeletal system, liver, kidneys, intestines, nervous system, heart, lungs, etc.

As is well known to those skilled in the art, the known and potential uses of IGF1 are diverse and extensive. For example, there have been many reports about the use of IGF1 as a potential therapeutic agent for treating neurodegenerative symptoms. For example, refer to Kanje et al., *Brain Res.*, 486:396-398 (1989); Hantai et al., *J. Neurol. Sci.*, 129:122-126 (1995); Contreras et al., *Pharmac. Exp. Therap.*, 274:1443-1499 (1995); Di Giulio et al., *Society for Neuroscience*, 22:1960 (1996); Di Giulio et al., *Society for Neuroscience*, 23:894 (1997); Hsu et al., *Biochem. Mol. Med.*, 60 (2): 142-148 (1997); Gorio et al., *Neuroscience*, 82:1029-1037 (1998). The IGF1 therapy is prescribed for a number of neurological symptoms such as ALS, stroke, epilepsy, Parkinson's disease, Alzheimer's disease, acute traumatic injury, aging, other disease- or injury-associated disorders, etc. For example, refer to U.S. Pat. Nos. 5,093, 137, 5,652,214 and 5,703,045; and International Patent Publication Nos. 1990-001483 and 1993-002695.

The uses of the IGF1 therapy for various other symptoms are stated in a number of published literatures. For example, refer to Schalch et al., "Short-term metabolic effects of recombinant human insulin-like growth factor I (rhIGF-I) in type II diabetes mellitus". Modern Concepts of Insulin-Like Growth Factors, Spencer, ed., New York: Elsevier Science Publ. Co. pp. 705-714 (1991); Clemmons and Underwood, *J. Clin. Endocrinol. Metab.*, 79 (1): 4-6 (1994); and Langford et al., *Eur. J. Clin. Invest.*, 23(9): 503-516 (1993) (for example, insulin resistance and diabetes are mentioned); O'shea et al., *Am. J. Physiol.*, 264: F917-F922 (1993) (for example, decreased kidney function is mentioned). Also, refer to U.S. Pat. No. 7,258,864 (for example, short stature is mentioned); U.S. Pat. Nos. 5,110,604 and 5,427,778 (for example, wound healing is mentioned); U.S. Pat. No. 5,126, 324 (for example, heart disorder and growth retardation are mentioned); U.S. Pat. No. 5,368,858 (for example, cartilage defect or injury is mentioned); U.S. Pat. Nos. 5,543,441 and 5,550,188 (for example, tissue augmentation is mentioned); U.S. Pat. No. 5,686,425 (for example, scar tissue, localized muscular dysfunction and urinary incontinence are mentioned); and U.S. Pat. No. 5,656,598 (for example, bone growth is mentioned). Also, refer to International Patent Publication No. 1991-012018 (for example, disorder in gut function is mentioned); International Patent Publication No. 1992-009301 and International Patent Publication No. 1992-014480 (for example, wound healing is mentioned); International Patent Publication No. 1993-008828 (for example, ischemia, hypoxia or neurodegeneration-associated nerve injury is mentioned); International Patent Publication No. 1994-016722 (for example, insulin resistance is mentioned); International Patent Publication No. 1996-002565 (for example, an IGF/IGFBP complex for promoting bone formation and regulating bone remodeling is mentioned); US Patent Publication No. 2003-0100505 (for example, osteoporosis is mentioned); and US Patent Publication No. 2005-0043240 (for example, obesity is mentioned).

The inventors of the present disclosure have researched to develop a gene therapeutic agent capable of achieving therapeutic effect even with a small amount of a gene. In doing so, they have identified that, when core-shell structured microparticles consisting of a halogenated hydrocarbon and/or halogenated sulfur as a core and a lipid component as an outer shell are administered in vivo along with a gene of the HGF, the IGF1, etc., the expression of the growth factor gene is increased remarkably, and have completed the present disclosure.

REFERENCES OF RELATED ART

Patent Documents (Patent document 001) KR 10-0562824 B.

DISCLOSURE

Technical Problem

The present disclosure is directed to providing a composition for increasing the expression of a growth factor gene, which contains core-shell structured microparticles as an active ingredient.

The present disclosure is also directed to providing a pharmaceutical composition for preventing or treating an ischemic disease, a neurological disease, a kidney disease or a liver disease, which contains the composition described above.

The present disclosure is also directed to providing a pharmaceutical composition for preventing or treating a symptom or a disease mediated by binding to the IGF1 receptor, which contains the composition described above.

Technical Solution

The present disclosure provides a composition for increasing the expression of a growth factor gene, which contains core-shell structured microparticles as an active ingredient, wherein the core is a halogenated hydrocarbon, halogenated sulfur or a mixture thereof as a biocompatible gas, and the shell is a lipid or a derivative thereof, and the growth factor gene is one or more genes selected from a human hepatocyte growth factor (HGF) gene, an isoform gene of the human hepatocyte growth factor and a variant gene thereof, or one or more genes selected from a human insulin-like growth factor 1 (IGF1) gene, an isoform gene of the human insulin-like growth factor 1 and a variant gene thereof.

In an exemplary embodiment of the present disclosure, the biocompatible gas may be selected from sulfur hexafluoride, octafluoropropane, bromochlorodifluoromethane, chlorodifluoromethane, dichlorodifluoromethane, bromotrifluoromethane, chlorotrifluoromethane, chloropentafluoroethane, dichlorotetrafluoroethane and a mixture thereof.

In an exemplary embodiment of the present disclosure, the halogenated hydrocarbon may be a perfluorinated hydrocarbon.

In an exemplary embodiment of the present disclosure, the perfluorinated hydrocarbon may be perfluoromethane, perfluoroethane, perfluoropropane, perfluorobutane, perfluoropentane, perfluorohexane, perfluoroheptane, perfluoropropene, perfluorobutene, perfluorobutadiene, perfluorobut-2-ene, perfluorocyclobutane, perfluoromethylcyclobutane, perfluorodimethylcyclobutane, perfluorotrimethylcyclobutane, perfluorocyclopentane, perfluorodimethylcyclopentane, perfluoromethylcyclopentane, perfluoromethylcyclohexane, perfluoromethylcyclohexane, perfluoromethylcyclohexane or a mixture thereof.

In an exemplary embodiment of the present disclosure, the lipid may be one or more selected from a group consisting of a simple lipid, a phospholipid, a glyceroglycolipid, a sphingoglycolipid, a cholesterol and a cationic lipid.

In an exemplary embodiment of the present disclosure, the phospholipid may be selected from a group consisting of a phosphatidylcholine derivative, a phosphatidylethanolamine derivative, a phosphatidylserine derivative, a diacetylated phospholipid, L-α-dioleyl phosphatidylethanolamine, diolein, phosphatidic acid, phosphatidylglycerol, phosphatidylinositol, lysophosphatidylcholine, sphingomyelin, a polyethylene glycolated phospholipid, egg yolk lecithin, soy lecithin and a hydrogenated phospholipid.

In an exemplary embodiment of the present disclosure, the glyceroglycolipid may be selected from a group consisting of sulfoxyribosyl glyceride, diglycosyl diglyceride, digalactosyl diglyceride, galactosyl diglyceride and glycosyl diglyceride.

In an exemplary embodiment of the present disclosure, the sphingoglycolipid may be galactosyl cerebroside, lactosyl cerebroside or ganglioside.

In an exemplary embodiment of the present disclosure, the cationic lipid may be selected from a group consisting of 1,2-dioleoyl-3-trimethylammonium propane (DOTAP), N-(2,3-dioleyloxypropan-1-yl)-N,N,N-trimethylammonium chloride (DOTMA), 2,3-dioleyloxy-N-[2-(sperminecarboxamido)ethyl]-N,N-dimethyl-1-propanaminium trifluoroacetate (DOSPA), 1,2-dimyristyloxypropyl-3-dimethylhydroxyethylammonium bromide (DMRIE), 1,2-dioleoyloxypropyl-3-diethylhydroxyethylammonium bromide (DORIE) and 3β-[N-(N'N'-dimethylaminoethylhy) carbamoyl]cholesterol (DC-Chol).

In an exemplary embodiment of the present disclosure, the variant gene of the human hepatocyte growth factor may be composed of any one selected from base sequences of SEQ IDS NO 3-6.

In an exemplary embodiment of the present disclosure, the composition may increase the expression of the growth factor gene by 30% or more.

The present disclosure also provides a pharmaceutical composition for preventing or treating an ischemic disease, a neurological disease, a kidney disease or a liver disease, which contains the composition described above and one or more genes selected from a human hepatocyte growth factor (HGF) gene, an isoform gene of the human hepatocyte growth factor and a variant gene thereof.

In the pharmaceutical composition for preventing or treating an ischemic disease, a neurological disease, a kidney disease or a liver disease, the human hepatocyte growth factor gene may be composed of a base sequence of SEQ ID NO 2, and the variant gene of the human hepatocyte growth factor may be composed of any one selected from base sequences of SEQ IDS NO 3-6.

The present disclosure also provides a pharmaceutical composition for preventing or treating a symptom or a disease mediated by binding to the IGF1 receptor, which contains the composition described above and one or more genes selected from a human insulin-like growth factor 1 (IGF1) gene, an isoform gene of the human insulin-like growth factor 1 and a variant gene thereof.

In the pharmaceutical composition for preventing or treating a symptom or a disease mediated by binding to the IGF1 receptor, the human insulin-like growth factor 1 gene may be composed of a base sequence of SEQ ID NO 7.

In an exemplary embodiment of the present disclosure, the symptom or disease may be selected from a group consisting of short stature, obesity, weight loss, cachexia, anorexia, neurodegenerative disorder, fibrosis-related condition, cartilage disorder, bone disease, inflammatory disorder, intestinal disorder, insulin resistance, diabetes, diabetic ketoacidosis, Rabson-Mendenhall syndrome, retinopathy, acromegaly, fibromuscular hyperplasia and heart disorder.

In an exemplary embodiment of the present disclosure, a subject in need of treatment of the short stature may be a human pediatric subject having insulin-like growth factor 1 deficiency (IGFD), and the composition may be effective to treat IGFD in the human pediatric subject.

Advantageous Effects

A composition for increasing the expression of a growth factor gene of the present disclosure may increase the expression of the growth factor gene by at least 30% or more when administered in vivo along with the gene (e.g., a polynucleotide encoding the gene or a vector including the same).

Especially, when administered along with at least one gene selected from a human hepatocyte growth factor (HGF) gene, an isoform gene of the human hepatocyte growth factor and a variant gene thereof, or at least one gene selected from a human insulin-like growth factor 1 (IGF1) gene, an isoform gene of the human insulin-like growth factor 1 and a variant gene thereof, which are appropriate for the present disclosure, the composition can increase the expression of the growth factor gene by at least 30%.

When administered along with a gene therapeutic agent, the composition can achieve a therapeutic effect even with a very small amount of a gene, and thus is useful.

BEST MODE

Figure 1:
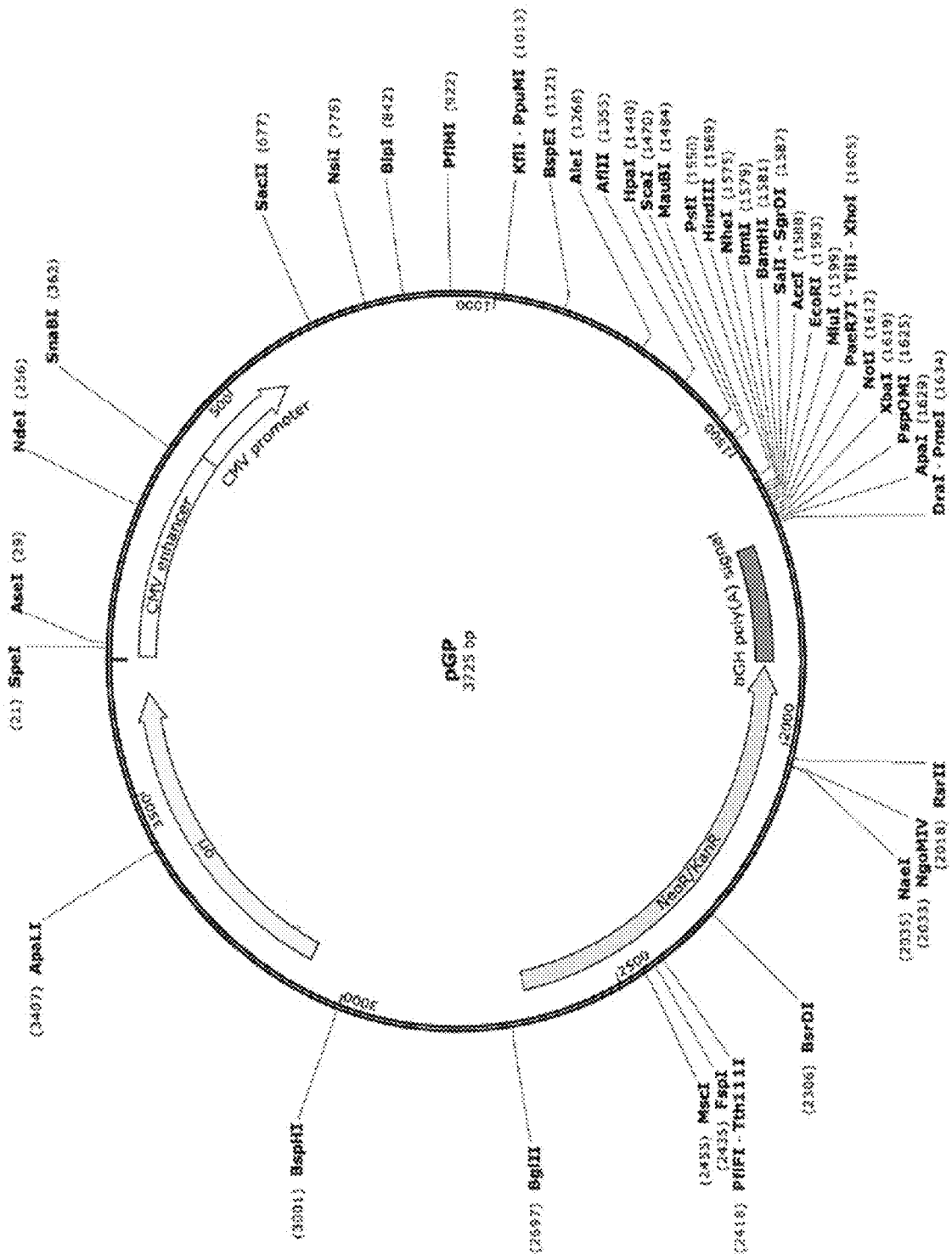
FIG. 1 shows the cleavage map of a pGP vector according to an exemplary embodiment of the present disclosure.

Hereinafter, the present disclosure is described in detail.

In an aspect, the present disclosure provides a composition for increasing the expression of a growth factor gene, which contains core-shell structured microparticles as an active ingredient, wherein the core is a halogenated hydrocarbon, halogenated sulfur or a mixture thereof as a biocompatible gas, and the shell is a lipid or a derivative thereof, and the growth factor gene is one or more genes selected from a human hepatocyte growth factor (HGF) gene, an isoform gene of the human hepatocyte growth factor and a variant gene thereof, or one or more genes selected from a human insulin-like growth factor 1 (IGF1) gene, an isoform gene of the human insulin-like growth factor 1 and a variant gene thereof.

Core

In the present disclosure, the "core" may be composed of a halogenated hydrocarbon, halogenated sulfur or a mixture thereof as a biocompatible gas.

The biocompatible gas may be sulfur hexafluoride, octafluoropropane, bromochlorodifluoromethane, chlorodifluoromethane, dichlorodifluoromethane, bromotrifluoromethane, chlorotrifluoromethane, chloropentafluoroethane, dichlorotetrafluoroethane or a mixture thereof.

Specifically, the halogenated hydrocarbon may be a perfluorinated hydrocarbon.

The perfluorinated hydrocarbon may be perfluoromethane, perfluoroethane, perfluoropropane, perfluorobutane, perfluoropentane, perfluorohexane, perfluoroheptane, perfluoropropene, perfluorobutene, perfluorobutadiene, perfluorobut-2-ene, perfluorocyclobutane, perfluoromethylcyclobutane, perfluorodimethylcyclobutane, perfluorotrimethylcyclobutane, perfluorocyclopentane, perfluoromethylcyclopentane, perfluorodimethylcyclopentane, perfluoromethylcyclohexane, perfluorodimethylcyclohexane, perfluoromethylcyclohexane or a mixture thereof.

Specifically, the biocompatible gas of the present disclosure may be sulfur hexafluoride or perfluorobutane.

Shell

In the present disclosure, the "shell" may be composed of a lipid or a derivative thereof.

The lipid may be one or more selected from a group consisting of a simple lipid, a phospholipid, a glyceroglycolipid, a sphingoglycolipid, a cholesterol and a cationic lipid. Specifically, it may be a phospholipid.

The phospholipid may be a phosphatidylcholine derivative, a phosphatidylethanolamine derivative, a phosphatidylserine derivative, diacetylated phospholipid, L-α-dioleyl phosphatidylethanolamine, diolein, phosphatidic acid, phosphatidylglycerol, phosphatidylinositol, lysophosphatidylcholine, sphingomyelin, polyethylene glycolated phospholipid, egg yolk lecithin, soy lecithin, a hydrogenated phospholipid, etc.

The glyceroglycolipid may be sulfoxyribosyl glyceride, diglycosyl diglyceride, digalactosyl diglyceride, galactosyl diglyceride, glycosyl diglyceride, etc.

The sphingoglycolipid may be galactosyl cerebroside, lactosyl cerebroside, ganglioside, etc.

And, the cationic lipid may be 1,2-dioleoyl-3-trimethylammonium propane (DOTAP), N-(2,3-dioleyloxypropan-1-yl)-N,N,N-trimethylammonium chloride (DOTMA), 2,3-dioleyloxy-N-[2-(sperminecarboxamido)ethyl]-N,
N-dimethyl-1-propanaminium trifluoroacetate (DOSPA), 1,2-dimyristyloxypropyl-3-dimethylhydroxyethylammonium bromide (DMRIE), 1,2-dioleoyloxypropyl-3-diethylhydroxyethylammonium bromide (DORIE), 3B-[N-(N'N'-dimethylaminoethylhy)carbamoyl]cholesterol (DC-Chol), etc.

Microparticles

The microparticles of the present disclosure are stabilized by the shell which surrounds the core gas. The shell retards the diffusion of a gas to nearby liquid and prevents fusion between the microparticles.

When administered in vivo, the microparticle retains its shape until it reaches a target cell or tissue, and releases the gas as it is destroyed near the target cell or tissue. The released gas may cause change in the cell membrane of the target cell and may facilitate the entry of the growth factor gene into the cytoplasmic environment of the target cell via the jet force of the gas.

The microparticles may have an average diameter of 1-10 µm, specifically 2-8 µm, more specifically 2-4 µm.

Composition for Increasing Gene Expression

Recently, there have been much research on core-shell microparticles having a gas as a core. In the previous research, the effect of increasing gene expression was not achieved unless ultrasound was irradiated together with the microparticles.

Specifically, Sang-Chol Lee et al., *Korean Circulation J* 2006; 36:32-38; "Enhancement of Gene Delivery into Mouse Skeletal Muscle with Microbubble Destruction by Low-Frequency Ultrasound" discloses that the effect of increasing gene expression is not achieved when only a luciferase gene-microparticles mixture is injected without irradiation of ultrasound.

Z P Shen et al., *Gene Therapy* (2008) 15, 1147-1155; "Ultrasound with microbubbles enhances gene expression of plasmid DNA in the liver via intraportal delivery" also discloses that the effect of increasing gene expression is not achieved when only a luciferase gene-microparticles mixture is injected without irradiation of ultrasound.

In addition, Xingsheng Li et al., *J Ultrasound Med* 2008; 27:453-460; "Experimental Research on Therapeutic Angiogenesis Induced by Hepatocyte Growth Factor Directed by Ultrasound-Targeted Microbubble Destruction in Rats" discloses that the effect of increasing gene expression is not achieved when only a HGF gene-liposome microparticles mixture is injected without irradiation of ultrasound.

However, the inventors of the present disclosure have identified that, while studying on the use of microparticles, the expression level of the HGF or IGF1 gene is increased remarkably even without ultrasound irradiation when the gene is injected along with the microparticles according to the present disclosure, and have completed the present disclosure. Meanwhile, as described specifically in test examples, the effect of increasing gene expression was not achieved with the microparticles for growth factor genes other than HGF or IGF1.

The composition for increasing the expression of a growth factor gene according to the present disclosure may increase the expression level of the growth factor gene by at least 30% when administered in vivo along with the gene.

Especially, when administered along with at least one gene selected from a human hepatocyte growth factor (HGF) gene, an isoform gene of the human hepatocyte growth factor and a variant gene thereof, or at least one gene selected from a human insulin-like growth factor 1 (IGF1) gene, an isoform gene of the human insulin-like growth factor 1 and a variant gene thereof, which are appropriate for the present disclosure, the composition can increase the expression of the gene by at least 30%, specifically 40% or more, more specifically 50% or more, most specifically 100% or more.

In the examples described below, it was verified that the composition for increasing the expression of a gene of the present disclosure increases the expression level of a HGF, HGFX7 or IGF1 gene remarkably when administered to mouse along with the HGF, HGFX7 or IGF1 gene. More specifically, the expression levels of HGF, HGFX7 and IGF1 were increased by 45% or more, 120% or more and 35% or more, respectively. Meanwhile, it was found out that the expression level of VEGF, FGF1, FGF4 or PDGF-B is not increased significantly even when administered to along with the composition for increasing the expression of a gene of the present disclosure. Specifically, the expression levels of VEGF, FGF4 and PDGF-B were increased only by up to 16%, up to 14% and up to 4%, respectively, and, the expression level of FGF1 was decreased by 40% or more, on the contrary.

That is to say, it seems that the composition for increasing the expression of a gene of the present disclosure is effective in increasing the expression level of a gene specifically only when administered along with one or more genes selected from human hepatocyte growth factor (HGF), an isoform thereof and a variant thereof or one or more genes selected from human insulin-like growth factor 1 (IGF1), an isoform thereof and a variant thereof, from among growth factor genes.

The composition may further contain a pharmaceutical adjuvant such as a stabilizer, a buffer, a salt for control of osmotic pressure, an excipient, an antiseptic, etc. or other therapeutically useful substances, and may be prepared into various formulations for oral or parenteral administration, specifically for parenteral administration, according to common methods. Specifically, a formulation for parenteral administration may be typically an injection formulation in the form of an isotonic aqueous solution or suspension. Alternatively, the composition may be prepared into a powder and then suspended in a solvent immediately before administration.

In the composition for increasing the expression of a gene of the present disclosure, the content of the microparticles may be 0.5-2,000 µL/mL, specially 1-1,000 µL/mL or 5-2,000 µg/mL, specifically 10-1,000 µg/mL, although not being particularly limited.

If the content of the microparticles is outside the above range, the desired effect cannot be achieved.

Specifically, the composition may be administered as a mixture with a gene to achieve a better effect.

Gene

The composition for increasing the expression of a gene according to the present disclosure may further increase the expression and efficiency of a gene when administered along with the following genes.

Human Hepatocyte Growth Factor (HGF) Gene

A human hepatocyte growth factor gene may be composed of a base sequence of SEQ ID NO 2. The human hepatocyte growth factor may be developed in the form of a gene therapeutic agent or in the form of a protein therapeutic agent.

Isoform of Human Hepatocyte Growth Factor

In the present disclosure, the "isoform of a human hepatocyte growth factor" refers to a HGF polypeptide having an amino acid sequence which is at least 80% identical to a HGF amino acid sequence naturally occurring in animals, including all allele variants. For example, a HGF isoform comprehends all of a normal form or wild type of HGF, and various variants (e.g., a splicing variant or a deletion variant) of HGF.

Variant Gene of Human Hepatocyte Growth Factor

In the present disclosure, the "variant gene of a human hepatocyte growth factor" may be a hybrid HGF gene capable of expressing two variants of HGF (HGF and dHGF) (see Korean Patent Registration No. 10-0562824). Specifically, the "hybrid HGF gene" refers to a hybrid HGF gene (SEQ ID NOS 3-5) expressing two types of variants HGF and dHGF (deleted variant of HGF) at the same time, having intron 4 of the human HGF gene or a fragment sequence thereof inserted between exon 4 and exon 5 of HGF cDNA and having high gene expression efficiency.

According to the gene therapeutic agent strategy of the present disclosure, using one or more nucleotide sequence encoding two or more types of HGF variants may be preferred in terms of therapeutic effect. The nucleotide sequence encoding two or more types of HGF variants may be provided as a single polynucleotide or an additional polynucleotide.

Also, in the present disclosure, the "variant gene of a human hepatocyte growth factor" may be HGFX6 (SEQ ID NO 3) (see Korean Patent Registration No. 10-0562824).

Also, in the present disclosure, the "variant gene of a human hepatocyte growth factor" may be HGFX7 (SEQ ID NO 4) (see Korean Patent Registration No. 10-0562824).

Also, in the present disclosure, the "variant gene of a human hepatocyte growth factor" may be HGFX8 (SEQ ID NO 5) (see Korean Patent Registration No. 10-0562824).

Also, in the present disclosure, the "variant gene of a human hepatocyte growth factor" may be a deleted variant of HGF (dHGF) (SEQ ID NO 6) (see Korean Patent Registration No. 10-0562824). The term "dHGF" used in the present disclosure refers to a deleted variant of the HGF protein produced from selective splicing of the HGF gene in animals, specifically in mammals. More specifically, it refers to a human HGF composed of 723 amino acids, with deletion of 5 amino acids (F, L, P, S and S) in the first kringle domain of the alpha chain from the full-length HGF sequence (728 amino acids).

Human Insulin-Like Growth Factor 1 (IGF1) Gene

A human insulin-like growth factor gene, particularly human insulin-like growth factor 1 (IGF1), may be composed of a base sequence of SEQ ID NO 7. The human insulin-like growth factor may be developed in the form of a protein therapeutic agent or in the form of a gene therapeutic agent.

IGF1 is mainly secreted by the liver as a result of stimulation by the human growth hormone (hGH). Nearly all the cells of the human body, particularly the cells in muscle, cartilage, bone, liver, kidney, nerve, skin and lung, are affected by IGF1. In addition to an insulin-like effect, IGF1 may also regulate cell growth.

Isoform of Human Insulin-Like Growth Factor 1

The term "IGF1 isoform (variant)" used in the present disclosure refers to an IGF1 polypeptide having an amino acid sequence which is at least 80% identical to an IGF1 amino acid sequence naturally occurring in animals, including all allele variants. For example, an IGF1 isoform comprehends all of a normal form or wild type of IGF1, and various variants (e.g., a splicing variant, a deletion variant or a substitution variant) of IGF1.

Specific examples of the IGF1 isoform include IGF1 Ea, IGF1 Eb, IGF1 Ec, etc.

Variant of Human Insulin-Like Growth Factor 1

In the present disclosure, the "IGF1 variant" may be a deleted variant of IGF1 (dIGF1) or an IGF1 variant with amino acid substitution at a specific position. The term "dIGF1" used in the present disclosure refers to a deleted variant of the IGF1 protein produced from selective splicing of the IGF1 gene in animals, specifically in mammals. As a specific example of the substitution variant of IGF1, the "IGF1 variant" may be a polypeptide wherein the amino acid glycine at position 42 is substituted with serine. As another specific example, the "IGF1 variant" may be a polypeptide with mutation in the amino acid G1, P2, E3, R36, R37, K68, S69 and/or A70 of the IGF1 protein.

Plasmid

The composition for increasing the expression of a gene according to the present disclosure can further increase the expression and efficiency of a gene when administered together with plasmids including single-chain polynucleotides encoding the gene.

In the present disclosure, the term "plasmid" generally refers to a circular DNA molecule operably linked to a vector, such that an exogenous gene can be expressed in a host cell. However, the plasmid may be used as a vector which is cleaved by a specific restriction enzyme and introduces a new target gene through gene recombination. Accordingly, the terms plasmid and vector are used interchangeably in the present disclosure, and those of ordinary skill in the field of genetic engineering will fully understand the context even if the terms are not distinguished.

In the present disclosure, the term "vector" refers to a DNA molecule which is capable of stably transporting an exogenous gene into a host cell. To be a useful vector, it must be replicable, have the means to enter the host cell, and be equipped with the means to detect its presence.

Expression

Expression Vector

The composition for increasing the expression of a gene according to the present disclosure can further increase the expression and efficiency of a gene when administered along with expression vectors including single-chain polynucleotides encoding the gene.

In the present disclosure, the term "expression" refers to generation of the gene in a cell.

In the present disclosure, the term "expression vector" refers to a vector capable of expressing a target gene in a suitable host, and means a gene construct including an essential regulatory element operably linked to express a gene insert.

In the present disclosure, the term "operably linked" means that a nucleic acid expression-regulating sequence and a polynucleotide encoding a target gene are functionally linked to perform a general function. For example, a promoter and a polynucleotide encoding the gene may be operably linked to affect the expression of the polynucleotide. The operable linkage to a recombinant vector may be prepared using a genetic recombinant technique well known in the art, and site-specific DNA cleavage and ligation may be achieved using enzymes generally known in the art.

The expression vector of the present disclosure may be prepared using a plasmid, a vector or a viral vector, although not being limited thereto. An appropriate expression vector may include an expression-regulating element such as a promoter, an operator, a start codon, a stop codon, a polyadenylation signal, an enhancer, etc. and may be prepared variously according to purposes. The promoter of the vector may be constitutive or inducible. Since a plasmid is the most commonly used form of a vector at present, the terms "plasmid" and "vector" are used sometimes interchangeably in the present disclosure. For the purpose of the present disclosure, it is preferred to use a plasmid vector. A typical plasmid vector that can be used for this purpose has a structure including (a) a replication origin for effective replication into several to hundreds of plasmid vectors per host cell and (b) a restriction enzyme site into which a fragment of foreign DNA can be inserted. Even if a proper restriction enzyme site does not exist, the vector and foreign DNA can be easily ligated using synthetic oligonucleotide adaptors or linkers according to common methods.

A vector used for overexpression of a gene according to the present disclosure may be an expression vector known in the art. A framework vector that may be used in the present disclosure may be selected from a group consisting of pCDNA3.1, pGP, pEF, pVAX, pUDK, pCK, pQE40, pT7, pET/Rb, pET28a, pET-22b(+) and pGEX, although not being particularly limited thereto. Specifically, use of a vector selected from a group consisting of pGP, pCK, pUDK and pVAX may be preferred in terms of effect.

In a specific exemplary embodiment, the expression vector of the present disclosure may be an expression vector including a pGP vector having a cleavage map of FIG. 1.

Pharmaceutical Composition

In another aspect, the present disclosure provides a pharmaceutical composition for preventing or treating an ischemic disease, a neurological disease, a kidney disease or a liver disease, which contains the composition for increasing the expression of a gene described above, a human hepatocyte growth factor (HGF) gene, an isoform gene of the human hepatocyte growth factor and a variant gene thereof. The pharmaceutical composition for preventing or treating an ischemic disease, a neurological disease, a kidney disease or a liver disease exhibits superior therapeutic effect since the expression of the gene is increased even with a small amount of the human hepatocyte growth factor (HGF), the isoform gene of the human hepatocyte growth factor or the variant gene thereof and, thus, can be usefully used to prevent or treat ischemic disease, neurological disease, kidney disease or liver disease.

The human hepatocyte growth factor gene may be composed of a base sequence of SEQ ID NO 2, and the variant gene of the human hepatocyte growth factor may be composed of any one selected from base sequences of SEQ IDS NO 3-6.

The "ischemic disease" may be selected from a group consisting of ischemic cerebrovascular disease, ischemic heart disease, ischemic myocardial Infarction, diabetic cardiovascular disease, ischemic heart failure, ischemic vascular disease, obstructive arteriosclerosis, myocardial hypertrophy, ischemic retinopathy, ischemic limb disease, ischemic colitis, ischemic acute renal failure, ischemic lung disease, ischemic stroke, ischemic necrosis, brain trauma, Alzheimer's disease, Parkinson's disease, neonatal hypoxia, glaucoma and diabetic peripheral neuropathy.

The "neurological disease" may be a central nervous system disease selected from a group consisting of amyotrophic lateral sclerosis (ALS), Alzheimer's disease, Parkinson's disease, Huntington's chorea, spinocerebellar degeneration, spinal cord injury, cerebral infarction, brain ischemia and multiple sclerosis.

The "kidney disease" may be acute renal failure or chronic renal failure.

The "liver disease" may be hepatic ischemia, fatty liver, hepatitis, liver cancer, hepatic fibrosis or liver cirrhosis.

In another aspect, the present disclosure provides a pharmaceutical composition for preventing or treating a symptom or a disease mediated by binding to the IGF1 receptor, which contains the composition for increasing the expression of a gene described above and one or more genes selected from a human insulin-like growth factor 1 (IGF1) gene, a variant gene of the human insulin-like growth factor 1 and a variant gene thereof. The pharmaceutical composition for preventing or treating a symptom or a disease mediated by binding to the IGF1 receptor exhibits superior therapeutic effect since the expression of the gene is increased even with a small amount of the human insulin-like growth factor 1 gene and, thus, can be usefully used to prevent or treat a symptom or a disease mediated by binding to the IGF1 receptor.

The human insulin-like growth factor 1 gene may be composed of a base sequence of SEQ ID NO 7.

In the pharmaceutical composition of the present disclosure, the composition for increasing the expression of a gene and the growth factor gene may be contained with a volume ratio of 1:0.5-30 (w/V).

The symptom or disease may be selected from a group consisting of short stature, obesity, weight loss, cachexia, anorexia, neurodegenerative disorder, fibrosis-related condition, cartilage disorder, bone disease, inflammatory disorder, intestinal disorder, insulin resistance, diabetes, diabetic ketoacidosis, Rabson-Mendenhall syndrome, retinopathy, acromegaly, fibromuscular hyperplasia and heart disorder.

Especially, a subject in need of treatment of the short stature may be a human pediatric subject having insulin-like growth factor 1 deficiency (IGFD), and the pharmaceutical composition of the present disclosure is very effective to treat IGFD in the human pediatric subject.

The pharmaceutical composition of the present disclosure may be for gene therapy.

Formulation

The pharmaceutical composition of the present disclosure may be prepared into pharmaceutical formulations for therapeutic purposes.

Pharmaceutical carriers and excipients and suitable pharmaceutical formulations are known in the art (e.g., "Pharmaceutical Formulation Development of Peptides and Proteins", Frokjaer et al., Taylor & Francis (2000) or "Handbook of Pharmaceutical Excipients", 3rd edition, Kibbe et al., Pharmaceutical Press (2000)). In particular, the pharmaceutical composition of the present disclosure may be formulated as a lyophilized form or a stable liquid form. The composition of the present disclosure may be freeze-dried through various procedures known in the art. The freeze-dried formulation is reconstituted by adding one or more pharmaceutically acceptable diluent such as sterile water for injection or sterile physiological saline.

The formulation of the composition is delivered to a subject via any pharmaceutical suitable means of administration. Various known delivery systems may be used to deliver the composition through any convenient routes. Mainly, the composition of the present disclosure is administered systemically. For systemic administration, the composition of the present disclosure is formulated for parenteral (e.g., intravenous, subcutaneous, intramuscular, intraperitoneal, intracerebral, intrapulmonary, intranasal or transdermal) delivery or enteral (e.g., oral, vaginal or rectal) delivery according to common methods. The most preferred routes of administration are intravenous and intramuscular routes. These formulations can be administered continuously by infusion or by bolus injection. Some formulations encompass slow release systems.

The composition of the present disclosure is administered to a patient in a therapeutically effective dose, meaning a dose that is sufficient to produce the desired effect, preventing or lessening the severity or spread of the condition or indication being treated without reaching a dose which produces intolerable adverse effects. The exact dose depends on many factors such as the indication, formulation, mode of administration, etc. and has to be determined through preclinical and clinical trials for each respective indication.

The pharmaceutical composition of the present disclosure may be administered either alone or in combination with other therapeutic agents. These agents may be incorporated as a part of the same pharmaceutical.

Treatment Method

The present disclosure also relates to a method for treating a subject suffering from ischemic disease, neurological disease, kidney disease or liver disease or a subject suffering from a symptom or a disease mediated by binding to the IGF1 receptor. The treatment method may include a step of administering an effective amount of the pharmaceutical composition of the present disclosure to the subject.

According to an exemplary embodiment of the present disclosure, the gene of HGF, IGF1, etc. of the present disclosure may be administered at a dose of 10 ng to 100 mg. When the administration of the HGF, IGF1 or a polynucleotide encoding the same is repeated more than once, the administration dose may be the same or different for each administration.

Hereinafter, the present disclosure is described in more detail through specific examples. However, the examples are only for illustrating the present disclosure in more detail and it will be obvious to those of ordinary skill in the art that the scope of the present disclosure is not limited by them.

EXAMPLES

Preparation of Materials
Genes
Human Hepatocyte Growth Factor (HGF) Gene

A gene of human hepatocyte growth factor (HGF) represented by SEQ ID NO 2 (see NCBI base sequence NM_000601.6) was synthesized by Genscript (USA).
Variant Gene of Human Hepatocyte Growth Factor (HGFX6)

A variant gene of the human hepatocyte growth factor represented by SEQ ID NO 3, HGFX6 (see Korean Patent Registration No. 10-0562824), was synthesized by Genscript (USA).
Variant Gene of the Human Hepatocyte Growth Factor (HGFX7)

A variant gene of the human hepatocyte growth factor represented by SEQ ID NO 4, HGFX7 (see Korean Patent Registration No. 10-0562824), was synthesized by Genscript (USA).
Variant Gene of the Human Hepatocyte Growth Factor (HGFX8)

A variant gene of the human hepatocyte growth factor represented by SEQ ID NO 5, HGFX8 (Korean Patent Registration No. 10-0562824), was synthesized by Genscript (USA).
Variant Gene of the Human Hepatocyte Growth Factor (dHGF)

A variant gene of the human hepatocyte growth factor represented by SEQ ID NO 6, dHGF (see Korean Patent Registration No. 10-0562824), was synthesized by Genscript (USA).
Human Insulin-Like Growth Factor 1 (IGF1) Gene Human insulin-like growth factor 1 gene represented by SEQ ID NO 7, IGF1 (see NCBI base sequence NM_001111283.2), was synthesized by Bionics (Korea).
Human Vascular Endothelial Growth Factor (VEGF) Gene Human vascular endothelial growth factor gene represented by SEQ ID NO 8 (see GenBank base sequence AB021221.1; $VEGF_{165}$), was synthesized by Bionics (Korea).
Human Fibroblast Growth Factor 1 (FGF1) Gene Human fibroblast growth factor 1 gene represented by SEQ ID NO 9, FGF1 (see GenBank base sequence X65778.1), was synthesized by Bionics (Korea).
Human Fibroblast Growth Factor 4 (FGF4) Gene Human fibroblast growth factor 4 gene represented by SEQ ID NO 10, FGF4 (see GenBank base sequence M17446.1), was synthesized by Bionics (Korea).
Human Platelet-Derived Growth Factor B (PDGF-B) Gene Human platelet-derived growth factor B gene represented by SEQ ID NO 11, PDGF-B (see GenBank base sequence X02811.1), was synthesized by Bionics (Korea).
Plasmids (pGP)

After synthesizing pCK plasmids referring to the literature of Lee et al. (Lee Y, et al. Improved expression of vascular endothelial growth factor by naked DNA in mouse skeletal muscles: implication for gene therapy of ischemic diseases. *Biochem. Biophys. Res. Commun.* 2000; 272 (1): 230-235), PCR was conducted in the same manner described in the literature using primers 1 and 2 of Table 1. After reacting the obtained fragments with EcoRI enzyme at 37° C. for 1 hour, DNA was purified using an Expin Gel SV (GeneAll, Korea) kit. Then, after conducting ligation for 30 minutes using T4 ligase, the DNA was incubated overnight with *E. coli*. Next day, after isolating DNA from the colony through mini-prep, pGP plasmids represented by SEQ ID NO 1 were obtained. FIG. 1 shows the cleavage map of the pGP vector according to an exemplary embodiment of the present disclosure.

TABLE 1

| Primer number | Primer name | Base sequence |
|---|---|---|
| 1 | pGP(F) | GACGAATTCACGCGTCTCGAGGCGGCCGCTC TAGAGGGCCCGTTTAAA |
| 2 | pGP(R) | GACGAATTCGTCGACGGATCCGCTAGCAAGCT TCGTGTCAAGGACGGT |

Preparation Example

Preparation of Plasmid DNAs Including Genes

Each of the genes and each of the pGP plasmids prepared above were cleaved with NheI and NotI enzymes for 1 hour and fragments were separated by conducting electrophoresis on agarose gel. The separated fragments were ligated for 30 minutes using T4 ligase and then incubated overnight with *E. coli*. Next day, DNA was isolated from the colony through mini-prep, and then digested with NheI and NotI. The cloned DNA was incubated overnight with an *E. coli* supernatant digested with restriction enzymes in a 4-L flask in the presence of kanamycin. Plasmid DNAs produced using an Endofree Giga prep. kit (Qiagen, USA) were used in animal experiments. The prepared plasmid DNAs are summarized in Table 2.

TABLE 2

| Gene | SEQ ID NO | Plasmid DNA |
|---|---|---|
| Human hepatocyte growth factor (HGF) | SEQ ID NO 2 | pGP-HGF |
| Variant of human hepatocyte growth factor (HGFX6) | SEQ ID NO 3 | pGP-HGFX6 |
| Variant of human hepatocyte growth factor (HGFX7) | SEQ ID NO 4 | pGP-HGFX7 |
| Variant of human hepatocyte growth factor (HGFX8) | SEQ ID NO 5 | pGP-HGFX8 |
| Variant of human hepatocyte growth factor (dHGF) | SEQ ID NO 6 | pGP-dHGF |
| Human insulin-like growth factor 1 (IGF1) | SEQ ID NO 7 | pGP-IGF1 |
| Human vascular endothelial growth factor (VEGF) | SEQ ID NO 8 | pGP-VEGF |
| Human fibroblast growth factor 1 (FGF1) | SEQ ID NO 9 | pGP-FGF1 |

TABLE 2-continued

| Gene | SEQ ID NO | Plasmid DNA |
|---|---|---|
| Human fibroblast growth factor 4 (FGF4) | SEQ ID NO 10 | pGP-FGF4 |
| Human platelet-derived growth factor B (PDGF-B) | SEQ ID NO 11 | pGP-PDGF-B |

Examples

Example 1: Preparation of Pharmaceutical Composition Containing Composition for Increasing Expression of Gene and HGF (HGF-MP1, HGF-MP2 and HGF-MP3)

Composition for Increasing Expression of Gene

Core-shell structured microparticles with a reference code of 62/400,210, having an average diameter of about 2.5 μm and composed of sulfur hexafluoride as a core and a lipid as a shell, were purchased from Bracco Imaging Korea (MP1). In addition, core-shell structured microparticles with a reference code of 64/630,0210, having an average diameter of about 2.4-3.6 μm and composed of perfluorobutane as a core and a shell including a lipid and a surfactant, were purchased from GE Healthcare Korea (MP2). In addition, core-shell structured microparticles with a reference code of 66/290, 0020, having an average diameter of about 1.1-3.3 μm and composed of perfluoropropane as a core and a shell including a lipid and a surfactant, were purchased from Bookyung SM (MP3).

A suspension (composition for increasing the expression of a gene) was prepared by mixing 225 μg of the microparticles MP1 with 2 mL of physiological saline according to the manufacturer's manual, and a suspension (composition for increasing the expression of a gene) was prepared by mixing 16 μL of MP2 with 2 ml of water for injection according to the manufacturer's manual. In addition, a suspension (composition for increasing the expression of a gene) was prepared by vigorously shaking a solution of the microparticles MP3 mixed with physiological saline (150 μL/mL) for 45 seconds according to the manufacturer's manual.

Preparation of Pharmaceutical Composition Containing Composition for Increasing Expression of Gene and HGF Pharmaceutical compositions HGF-MP1, HGF-MP2 and HGF-MP3 were prepared by mixing 15 μL of the compositions for increasing the expression of a gene (MP1, MP2 and MP3), respectively, with the pGP-HGF prepared above (70 μg/35 μL).

Example 2: Preparation of Pharmaceutical Composition Containing Composition for Increasing Expression of Gene and HGFX7 (HGFX7-MP1 and HGFX7-MP2)

Composition for Increasing Expression of Gene

Compositions for increasing the expression of a gene were prepared in the same manner as in Example 1.

Preparation of Pharmaceutical Composition Containing Composition for Increasing Expression of Gene and HGFX7

Pharmaceutical compositions HGFX7-MP1 and HGFX7-MP2 were prepared by mixing 15 μL of the compositions for increasing the expression of a gene (MP1 and MP2), respectively, with the pGP-HGFX7 prepared above (70 μg/35 μL).

Example 3: Preparation of Pharmaceutical Composition Containing Composition for Increasing Expression of Gene and IGF1 (IGF1-MP1, IGF1-MP2 and IGF1-MP3)

Composition for Increasing Expression of Gene

Compositions for increasing the expression of a gene were prepared in the same manner as in Example 1.

Preparation of Pharmaceutical Composition Containing Composition for Increasing Expression of Gene and IGF1

Pharmaceutical compositions IGF1-MP1, IGF1-MP2 and IGF1-MP3 were prepared by mixing 15 μL of the compositions for increasing the expression of a gene (MP1, MP2 and MP3), respectively, with the pGP-IGF1 prepared above (70 μg/35 μL).

Comparative Example 1: Preparation of Pharmaceutical Composition Containing Composition for Increasing Expression of Gene and VEGF (VEGF-MP1 and VEGF-MP2)

Composition for Increasing Expression of Gene

Compositions for increasing the expression of a gene were prepared in the same manner as in Example 1.

Preparation of Pharmaceutical Composition Containing Composition for Increasing Expression of Gene and VEGF Pharmaceutical compositions VEGF-MP1 and VEGF-MP2 were prepared by mixing 15 μL of the compositions for increasing the expression of a gene (MP1 and MP2), respectively, with the pGP-VEGF prepared above (70 μg/35 μL).

Comparative Example 2: Preparation of Pharmaceutical Composition Containing Composition for Increasing Expression of Gene and FGF1 (FGF1-MP1 and FGF1-MP2)

Composition for Increasing Expression of Gene

Compositions for increasing the expression of a gene were prepared in the same manner as in Example 1.

Preparation of Pharmaceutical Composition Containing Composition for Increasing Expression of Gene and FGF1

Pharmaceutical compositions FGF1-MP1 and FGF1-MP2 were prepared by mixing 15 μL of the compositions for increasing the expression of a gene (MP1 and MP2), respectively, with the pGP-FGF1 prepared above (70 μg/35 μL).

Comparative Example 3: Preparation of Pharmaceutical Composition Containing Composition for Increasing Expression of Gene and FGF4 (FGF4-MP1 and FGF4-MP2)

Composition for Increasing Expression of Gene

Compositions for increasing the expression of a gene were prepared in the same manner as in Example 1.

Preparation of Pharmaceutical Composition Containing Composition for Increasing Expression of Gene and FGF4

Pharmaceutical compositions FGF4-MP1 and FGF4-MP2 were prepared by mixing 15 μL of the compositions for increasing the expression of a gene (MP1 and MP2), respectively, with the pGP-FGF4 prepared above (70 μg/35 μL).

Comparative Example 4: Preparation of Pharmaceutical Composition Containing Composition for Increasing Expression of Gene and PDGF-B (PDGF-B-MP1 and PDGF-B-MP2)

Composition for Increasing Expression of Gene

Compositions for increasing the expression of a gene were prepared in the same manner as in Example 1.

Preparation of Pharmaceutical Composition Containing Composition for Increasing Expression of Gene and PDGF-B Pharmaceutical compositions PDGF-B-MP1 and PDGF-B-MP2 were prepared by mixing 15 µL of the compositions for increasing the expression of a gene (MP1 and MP2), respectively, with the pGP-PDGF-B prepared above (70 µg/35 µL).

Control Group

Composition for Increasing Expression of Gene

A suspension (corresponding to a composition for increasing the expression of a gene) was prepared by mixing 128 µL of in vivo JetPEI (Polyplus, USA) with 2 mL of 5% glucose according to the manufacturer's manual.

Preparation of Pharmaceutical Composition Containing Composition for Increasing Expression of Gene and Each Gene Pharmaceutical compositions HGF-JetPEI, HGFX7-JetPEI, IGF1-JetPEI and VEGF-JetPEI were prepared by mixing 15 µL of the composition for increasing the expression of a gene with DNAs (70 µg/35 µL).

Test Examples

Test Example 1: Expression Level of Protein in Mouse

Each of the pharmaceutical compositions according to the control group, examples and comparative examples was injected into the lower calf muscle of Balb/c mouse (Samtako Bio) with 75 µg/50 µL/leg.

On day 7 after the administration, the mouse was sacrificed and the muscle at the injected area was excised. Then, total proteins were isolated after grinding the excised muscle using liquid nitrogen and a protein extraction kit (Cell Biolabs, USA). The amounts of the isolated total proteins were measured using a DC protein assay kit (Bio-Rad laboratories, USA).

For measurement of the HGF protein, the expression level of each gene was measured using an ELISA kit (R&D Systems, USA) for the same amount of protein. The result is shown in FIG. 2 and FIG. 3.

For measurement of the IGF1 protein, the expression level of each gene was measured using an IGF1 ELISA kit (R&D Systems, USA) for the same amount of protein. The result is shown in FIG. 4.

Figure 2:
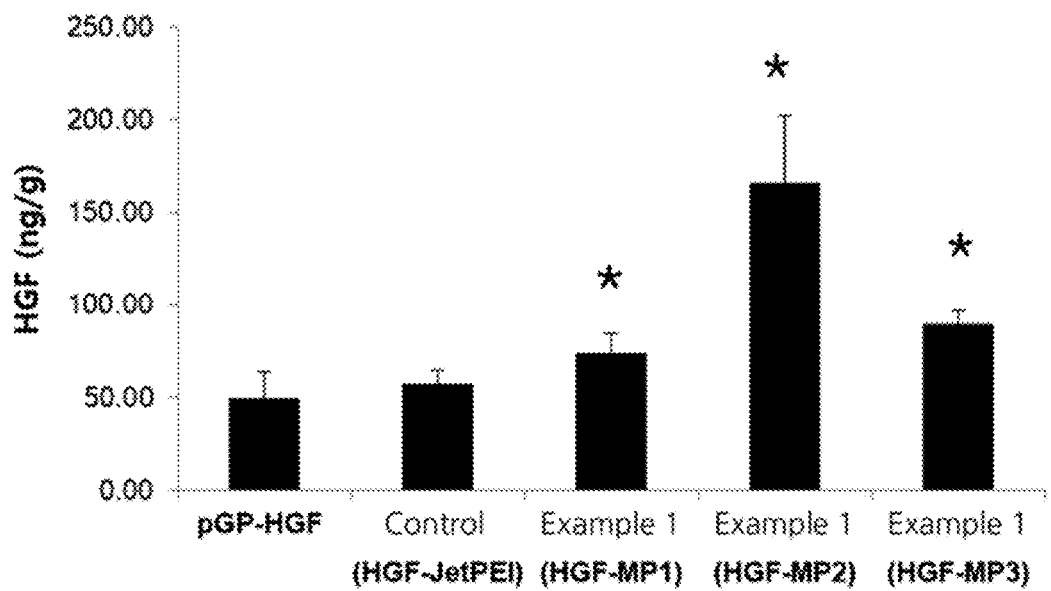
FIG. 2 compares the expression level of the HGF protein depending on the administration of pGP-HGF (gene only), a pharmaceutical composition of a control group (HGF-JetPEI) and pharmaceutical compositions according to Example 1 (HGF-MP1, HGF-MP2 and HGF-MP3) in mouse.
Figure 3:
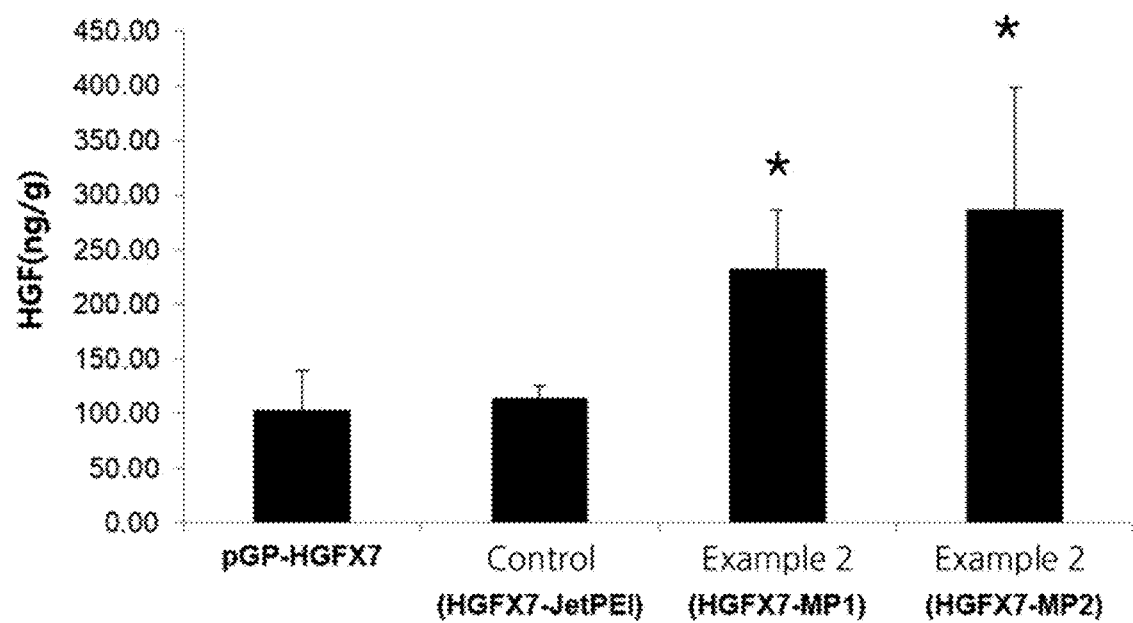
FIG. 3 compares the expression level of the HGF protein depending on the administration of pGP-HGFX7 (gene only), a pharmaceutical composition of a control group (HGFX7-JetPEI) and pharmaceutical compositions according to Example 2 (HGFX7-MP1 and HGFX7-MP2) in mouse.
Figure 4:
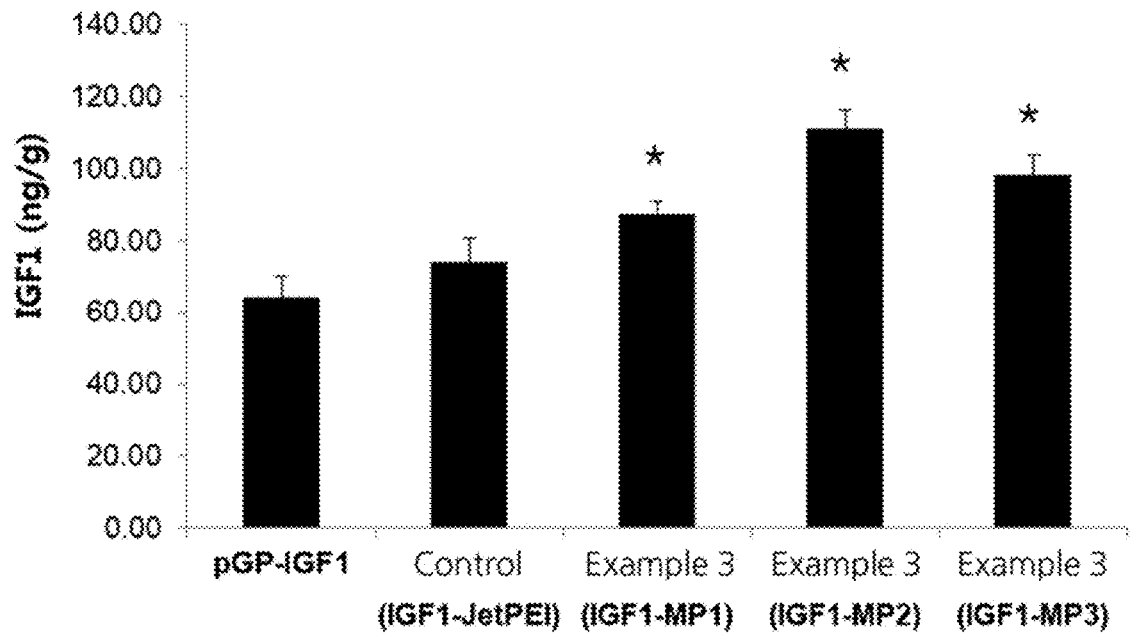
FIG. 4 compares the expression level of the IGF1 protein depending on the administration of pGP-IGF1 (gene only), a pharmaceutical composition of a control group (IGF1-JetPEI) and pharmaceutical compositions according to Example 3 (IGF1-MP1, IGF1-MP2 and IGF1-MP3) in mouse.

From FIGS. 2-4, it can be seen that the administration of the pharmaceutical compositions according to the present disclosure (Examples 1-3) resulted in statistically significant high expression level of HGF or IGF1 gene as compared to the composition of the control group.

Figure 5:
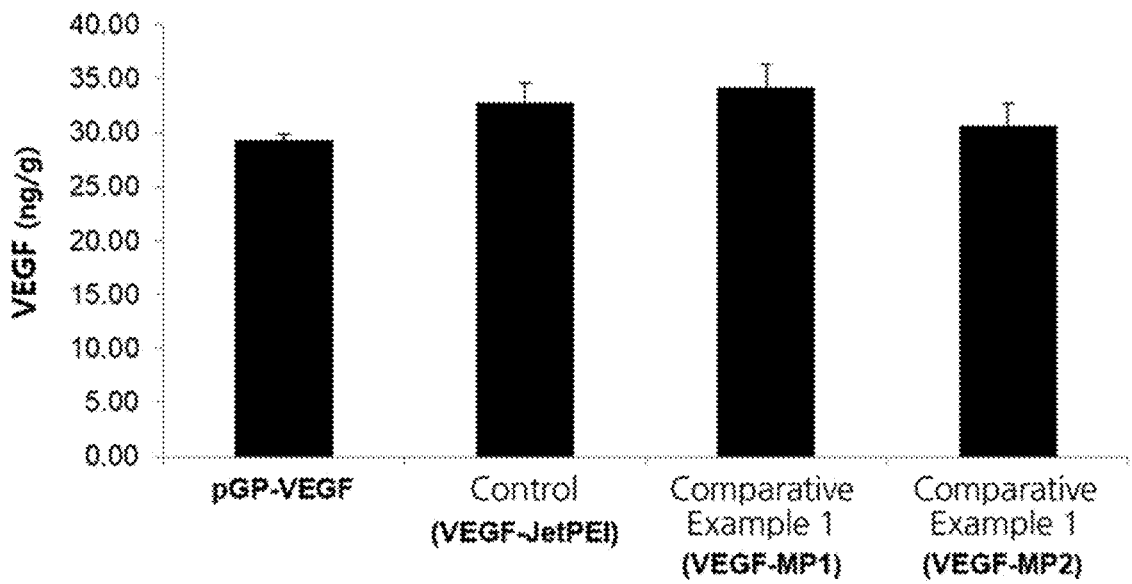
FIG. 5 compares the expression level of the VEGF protein depending on the administration of pGP-VEGF (gene only), a pharmaceutical composition of a control group (VEGF-JetPEI) and pharmaceutical compositions according to Comparative Example 1 (VEGF-MP1 and VEGF-MP2) in mouse.

For measurement of the VEGF protein, the expression level of each gene was measured using a VEGF ELISA kit (R&D Systems, USA) for the same amount of protein. The result is shown in FIG. 5.

Figure 6:
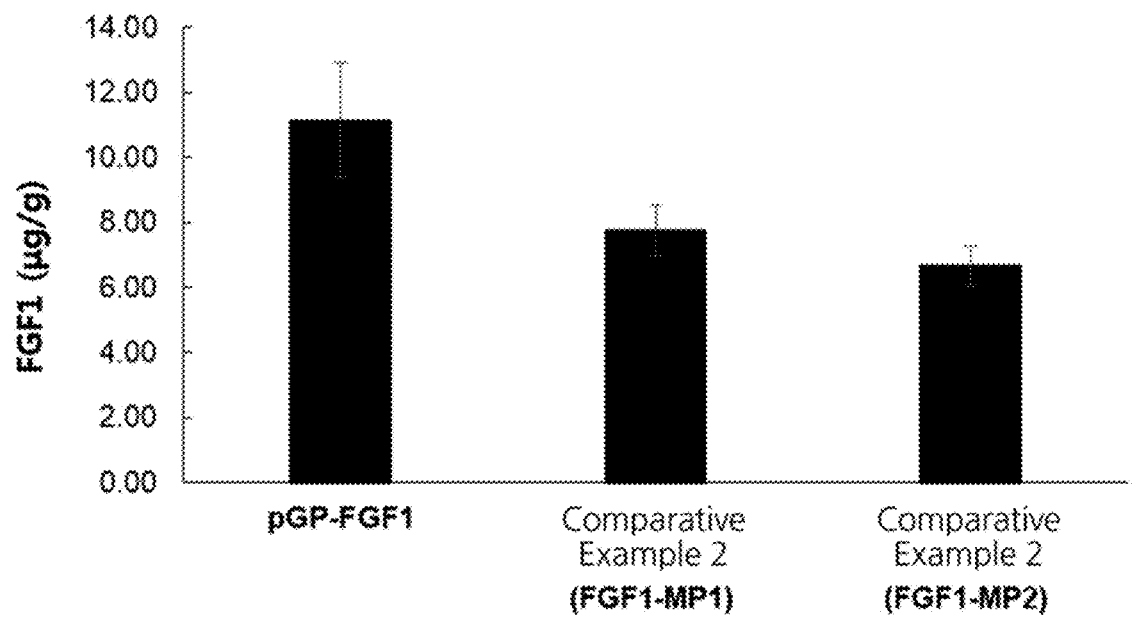
FIG. 6 compares the expression level of the FGF1 protein depending on the administration of pGP-FGF1 (gene only) and pharmaceutical compositions according to Comparative Example 2 (FGF1-MP1 and FGF1-MP2) in mouse.

For measurement of the FGF1 protein, the expression level of each gene was measured using a FGF1 ELISA kit (Abcam, USA) for the same amount of protein. The result is shown in FIG. 6.

Figure 7:
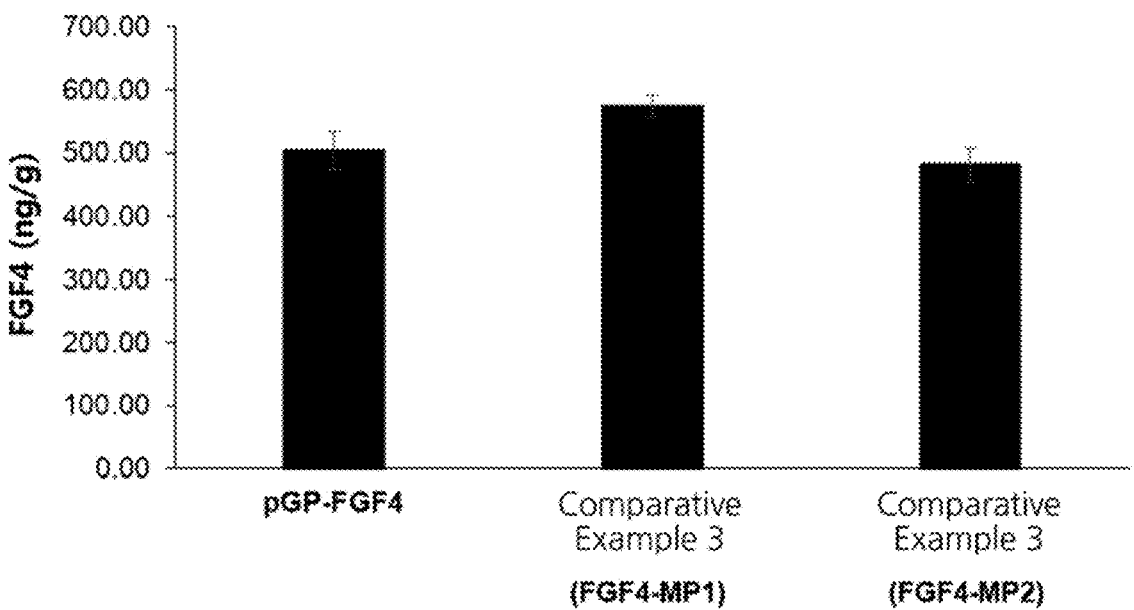
FIG. 7 compares the expression level of the FGF4 protein depending on the administration of pGP-FGF4 (gene only) and pharmaceutical compositions according to Comparative Example 3 (FGF4-MP1 and FGF4-MP2) in mouse.

For measurement of the FGF4 protein, the expression level of each gene was measured using a FGF4 ELISA kit (Abcam, USA) for the same amount of protein. The result is shown in FIG. 7.

Figure 8:
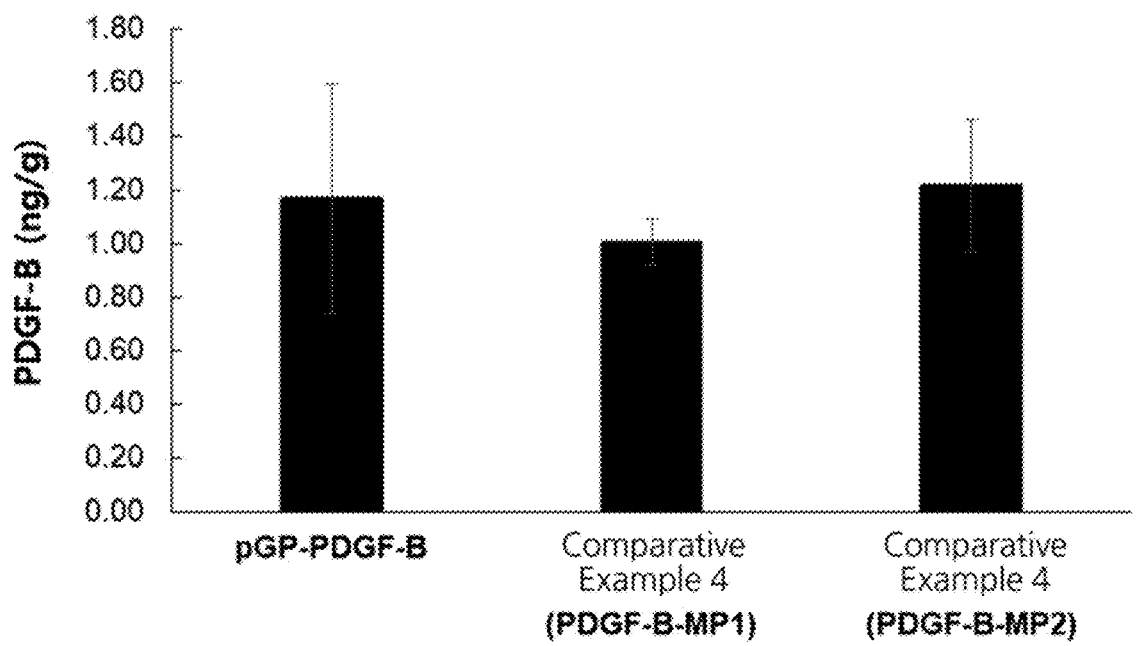
FIG. 8 compares the expression level of the PDGF-B protein depending on the administration of pGP-PDGF-B (gene only) and pharmaceutical compositions according to Comparative Example 4 (PDGF-B-MP1 and PDGF-B-MP2) in mouse.

For measurement of the PDGF-B protein, the expression level of each gene was measured using a PDGF-B ELISA kit (R&D Systems, USA) for the same amount of protein. The result is shown in FIG. 8.

From FIGS. 5-8, it can be seen that the administration of the compositions of Comparative Examples 1-4 did not resulted in significant increase in expression levels as compared to the composition of the control group.

These results confirm that the compositions of Examples 1-3 according to the present disclosure can significantly increase the expression level of the HGF or IGF1 gene.

Test Example 2: Evaluation of Effect of Pharmaceutical Composition of Present Disclosure in Diabetes-Induced Rat Peripheral Neuropathy Model Diabetic peripheral neuropathy (DPN) is a complex disease of ischemic disease and neurological disease which is induced by peripheral nerve damage caused by diabetes-induced increase in blood sugar and damage to microvessels and accompanied by clinical pain. Streptozotocin-induced diabetic peripheral neuropathy was used as a representative animal model.

Type 1 diabetes was induced in 6-week-old male Sprague-Dawley rats purchased from Samtako Bio by intravenously injecting 70 mg/kg streptozotocin (STZ). One week after the STZ injection, subjects with non-fasting glucose levels of 300 mg/dL or higher were selected. For each subject, paw withdrawal threshold (PWT) was measured by manual Von Frey test in order to evaluate the degree of pain. The subjects in which pain was induced (PWT values of 4.0 or below) were selected and divided into two groups of 5 rats per group.

For a control group, 400 µg of pGP-HGFX7 DNA was administered into calf muscles on both sides with 200 µg/200 µL, respectively. For a test group, the same amount (400 µg) of HGFX7-MP2 of Example 2 was administered into calf muscles on both sides.

Figure 9:
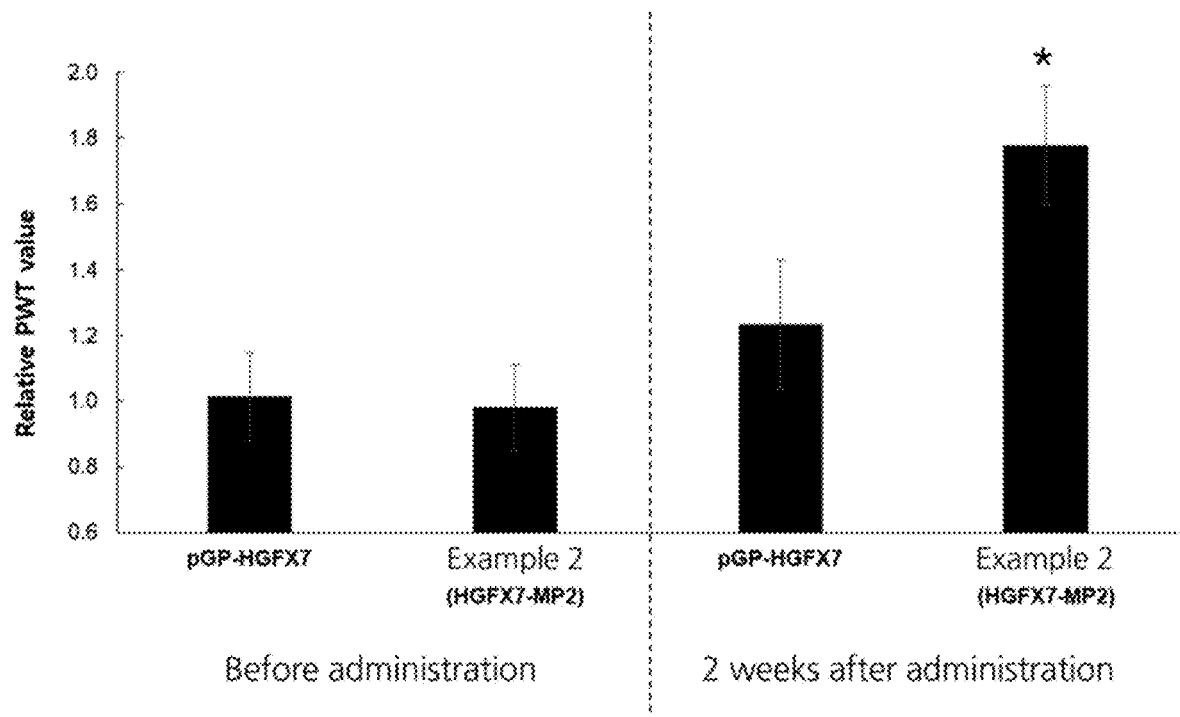
FIG. 9 shows that the PWT value is increased remarkably 2 weeks after the administration of a composition of Example 2 (HGFX7-MP2) of the present disclosure to a diabetes-induced rat peripheral neuropathy model.

PWT was measured as a degree of pain 2 weeks after the administration. As a result, it was confirmed that the PWT value was increased statistically significantly in the group to which the HGFX7-MP2 of Example 2 was administered as compared to the control group (see FIG. 9).

Test Example 3: Evaluation of Efficacy of Pharmaceutical Composition of Present Disclosure in Chronic Constriction Injury-Induced Rat Neuropathy Model Neuropathic pain is known as a chronic neurological disease caused by anomaly in the nervous system and may be clinically associated with allodynia, etc. due to increased sensitivity to pain. Chronic constriction injury induced by sciatic ligation was used as a representative animal model of the chronic neuropathic pain.

5-week-old male Sprague-Dawley rats purchased from Orient Bio were anesthetized by inhalation of a mixture of isoflurane, nitrogen dioxide and oxygen, and the sciatic nerve was exposed by incision of the left femoral region. The exposed sciatic nerve was loosely ligated with three strands of 4-0 catgut suture with a spacing of 1.0-1.5 mm and then stitched. One week after the surgery, paw withdrawal threshold (PWT) was measured by manual Von Frey test, and the subjects in which pain was induced (PWT values of 4.0 or below) were selected and divided into two groups of 5 rats per group.

For a control group, 1 mg of pGP-HGF DNA was administered into four areas of the left femoral muscle with 250 µg/250 µL. For a test group, the same amount (1 mg) of HGF-MP2 of Example 1 was administered into the same areas as the control group with 250 μg/250 μL.

Figure 10:
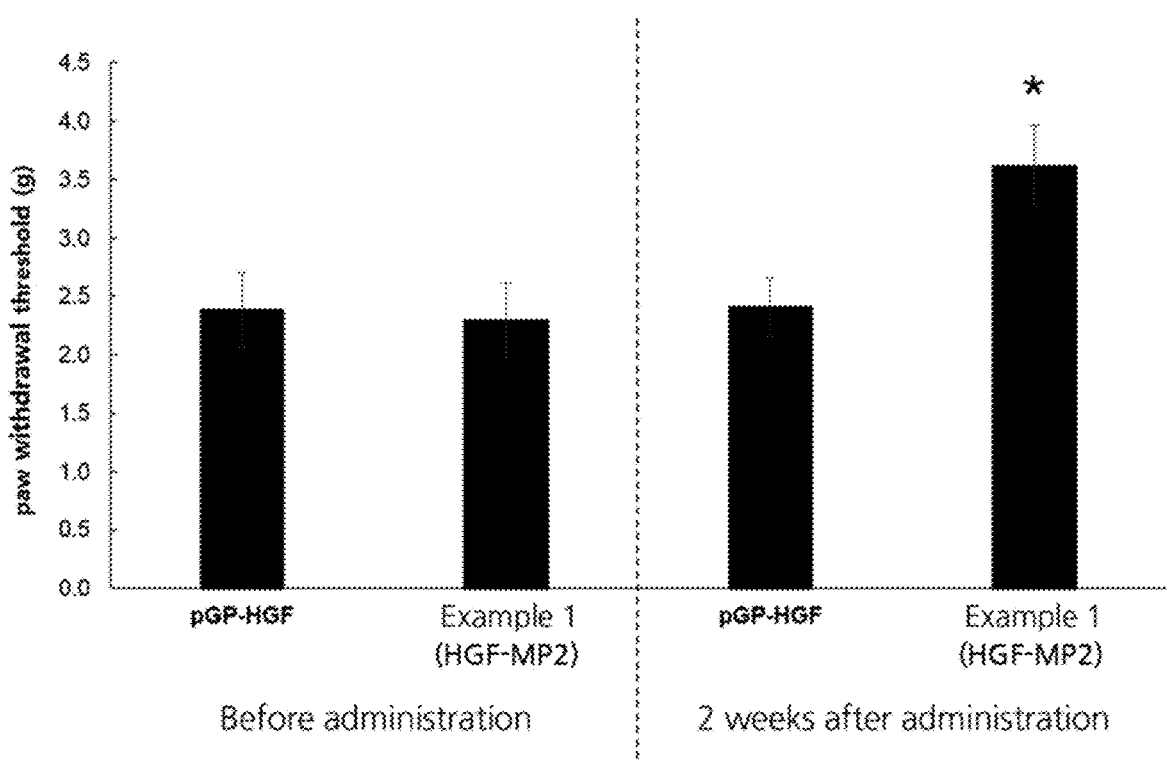
FIG. 10 shows that the PWT value is increased remarkably 2 weeks after the administration of a composition of Example 1 (HGF-MP2) to a chronic constriction injury-induced rat neuropathy model.

PWT was measured as a degree of pain 2 weeks after the administration. As a result, it was confirmed that the PWT value was increased statistically significantly in the group to which the HGF-MP2 of Example 1 was administered as compared to the control group, meaning that the magnitude of stimulation required for sensing pain was increased significantly (see FIG. 10).

Through these results, it was verified that the composition of the present disclosure can enhance the efficacy of genes in several disease models by significantly increasing the expression level of the genes.

Specifically, as a result of administering the composition for increasing the expression of a gene of the present disclosure along with HGFX7 to the diabetic neuropathy-induced rat model in Test Example 2 and then measuring the PWT value 2 weeks later, it was confirmed that the PWT value was increased by about 80% as compared to the control group.

In addition, as a result of administering the composition for increasing the expression of a gene of the present disclosure along with HGF to the neuropathic pain-induced rat model in Test Example 3 and then measuring the PWT value 2 weeks later, it was confirmed that the PWT value was increased by 40% or more as compared to the control group.

The increase in the PWT value means that the magnitude of stimulation required for sensing pain was increased significantly, i.e., pain was relieved. It seems that the effect of relieving pain in the diabetic neuropathy- or neuropathic pain-induced rat model is owing to the increased expression of HGF or HGFX7 by the composition for increasing the expression of a gene of the present disclosure.

That is to say, through the test examples described above, it was confirmed that a pharmaceutical composition containing the composition for increasing the expression of a gene of the present disclosure and one or more genes selected from a human hepatocyte growth factor (HGF) gene, an isoform gene of the human hepatocyte growth factor and a variant gene thereof is effective in relieving pain in both the neuropathic pain-induced rat model and the diabetic neuropathy-induced rat model. Accordingly, it is thought that a pharmaceutical composition containing the composition for increasing the expression of a gene of the present disclosure and one or more genes selected from a human hepatocyte growth factor (HGF) gene, an isoform gene of the human hepatocyte growth factor and a variant gene thereof as an active ingredient can be used to prevent, ameliorate or treat various neurological diseases such as diabetic neuropathy, neuropathic pain, etc.

Although the present disclosure was illustrated with the specific exemplary embodiments described above, various modifications or changes can be made thereto without departing from the subject matter and scope of the present disclosure. In addition, such modifications or changes within the subject matter of the present disclosure are included in the scope of the appended claims.

The invention claimed is:

1. A method for preventing or treating an ischemic disease, a neurological disease, a kidney disease or a liver disease in a subject in need thereof via increasing expression of one or more genes selected from a human hepatocyte growth factor (HGF) gene, an isoform gene of the human hepatocyte growth factor and a variant gene of the human hepatocyte growth factor, comprising administering to the subject a composition comprising the one or more genes and core-shell structured microparticles as active ingredients, and
wherein the core is perfluorobutane, sulfur hexafluoride, or a mixture thereof as a biocompatible gas, and the shell is a lipid or a derivative thereof.

2. The method for preventing or treating an ischemic disease, a neurological disease, a kidney disease or a liver disease according to claim 1, wherein the human hepatocyte growth factor gene is composed of a base sequence of SEQ ID NO 2.

3. The method for preventing or treating an ischemic disease, a neurological disease, a kidney disease or a liver disease according to claim 1, wherein the variant gene of the human hepatocyte growth factor is composed of any one selected from base sequences of SEQ IDS NO 3-6.

4. The method according to claim 1, wherein the pharmaceutical composition is a suspension, the suspension comprising the one or more genes and the core-shell structured microparticles.

5. The method according to claim 1, wherein the core-shell structured microparticles have an average diameter of 2.4-3.6 μm.

* * * * *

SEQUENCE LISTING

```
<160> NUMBER OF SEQ ID NOS: 11

<210> SEQ ID NO 1
<211> LENGTH: 3725
<212> TYPE: DNA
<213> ORGANISM: Artificial Sequence
<220> FEATURE:
<223> OTHER INFORMATION: nucleotide sequence of pGP

<400> SEQUENCE: 1
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtccgcccc ctattgacgt caatgacggt aaatggcccg     300
cctggcatta tgcccagtac atgaccttac gggactttcc tacttggcag tacatctacg     360
tattagtcat cgctattacc atggtgatgc ggttttggca gtacaccaat gggcgtggat     420
agcggtttga ctcacgggga tttccaagtc tccaccccat tgacgtcaat gggagtttgt     480
tttggcacca aaatcaacgg gactttccaa aatgtcgtaa taaccccgcc ccgttgacgc     540
aaatgggcgg taggcgtgta cggtgggagg tctatataag cagagctcgt ttagtgaacc     600
gtcagatcgc ctggagacgc catccacgct gttttgacct ccatagaaga cccgggacc     660 gatccagcct ccgcggccgg gaacggtgca ttggaacgcg gattccccgt gccaagagtg     720
acgtaagtac cgcctataga ctctataggc acacccttt ggctcttatg catgctatac     780 tgttttggc ttggggccta tacaccccg cttccttatg ctaggtga tggtatagct     840 tagcctatag gtgtgggtta ttgaccatta ttgaccactc ccctattggt gacgatactt     900
```

```
tccattacta atccataaca tggctctttg ccacaactat ctctattggc tatatgccaa   960
tactctgtcc ttcagagact gacacggact ctgtatttt  acaggatggg gtcccattta  1020
ttatttacaa attcacatat acaacaacgc cgtcccccgt gcccgcagtt tttattaaac  1080
atagcgtggg atctccacgc gaatctcggg tacgtgttcc ggacatgggc tcttctccgg  1140
tagcggcgga gcttccacat ccgagccctg gtcccatgcc tccagcggct catggtcgct  1200
cggcagctcc ttgctcctaa cagtggaggc cagacttagg cacagcacaa tgcccaccac  1260
caccagtgtg ccgcacaagg ccgtggcggt agggtatgtg tctgaaaatg agctcggaga  1320
ttgggctcgc accgctgacg cagatggaag acttaaggca gcggcagaag aagatgcagg  1380
cagctgagtt gttgtattct gataagagtc agaggtaact cccgttgcgg tgctgttaac  1440
ggtggagggc agtgtagtct gagcagtact cgttgctgcc gcgcgcgcca ccagacataa  1500
tagctgacag actaacagac tgttcctttc catgggtctt ttctgcagtc accgtccttg  1560
acacgaagct tgctagcgga tccgtcgacg aattcacgcg tctcgaggcg gccgctctag  1620
agggcccgtt taaacccgct gatcagcctc gactgtgcct tctagttgcc agccatctgt  1680
tgtttgcccc tccccgtgc  cttccttgac cctggaaggt gccactccca ctgtcctttc  1740
ctaataaaat gaggaaattg catcgcattg tctgagtagg tgtcattcta ttctgggggg  1800
tggggtgggg caggacagca agggggagga ttgggaagac aatagcaggc atgctgggga  1860
gtcgaaattc agaagaactc gtcaagaagg cgatagaagg cgatgcgctg cgaatcggga  1920
gcggcgatac cgtaaagcac gaggaagcgg tcagcccatt cgccgccaag ctcttcagca  1980
atatcacggg tagccaacgc tatgtcctga tagcggtccg ccacacccag ccggccacag  2040
tcgatgaatc cagaaaagcg gccattttcc accatgatat tcggcaagca ggcatcgcca  2100
tgggtcacga cgagatcctc gccgtcgggc atgctcgcct tgagcctggc gaacagttcg  2160
gctggcgcga gcccctgatg ctcttcgtcc agatcatcct gatcgacaag accggcttcc  2220
atccgagtac gtgctcgctc gatgcgatgt ttcgcttggt ggtcgaatgg gcaggtagcc  2280
ggatcaagcg tatgcagccg ccgcattgca tcagccatga tggatacttt ctcggcagga  2340
gcaaggtgag atgacaggag atcctgcccc ggcacttcgc ccaatagcag ccagtccctt  2400
cccgcttcag tgacaacgtc gagcacagct gcgcaaggaa cgcccgtcgt ggccagccac  2460
gatagccgcg ctgcctcgtc ttgcagttca ttcagggcac cggacaggtc ggtcttgaca  2520
aaaagaaccg ggcgcccctg cgctgacagc cggaacacgg cggcatcaga gcagccgatt  2580
gtctgttgtg cccagtcata gccgaatagc ctctccaccc aagcggccgg agaacctgcg  2640
tgcaatccat cttgttcaat catgcgaaac gatcctcatc ctgtctcttg atcagatctt  2700
gatcccctgc gccatcagat ccttggcggc gagaaagcca tccagtttac tttgcagggc  2760
ttcccaactt accagagggc gccccagctg gcaattccgg ttcgcttgct gtccataaaa  2820
ccgcccagtc tagctatcgc catgtaagcc cactgcaagc tacctgcttt ctctttgcgc  2880
ttgcgttttc ccttgtccag atagcccagt agctgacatt catccggggt cagcaccgtt  2940
tctgcggact ggctttctac gtgaaaagga tctaggtgaa gatcctttt  gataatctca  3000
tgaccaaaat cccttaacgt gagttttcgt tccactgagc gtcagacccc gtagaaaaga  3060
tcaaaggatc ttcttgagat cctttttttc tgcgcgtaat ctgctgcttg caaacaaaaa  3120
aaccaccgct accagcggtg gtttgtttgc cggatcaaga gctaccaact ctttttccga  3180
aggtaactgg cttcagcaga gcgcagatac caaatactgt ccttctagtg tagccgtagt  3240
taggccacca cttcaagaac tctgtagcac cgcctacata cctcgctctg ctaatcctgt  3300
```

```
taccagtggc tgctgccagt ggcgataagt cgtgtcttac cggggttggac tcaagacgat   3360 agttaccgga taaggcgcag cggtcgggct gaacgggggg ttcgtgcaca cagcccagct   3420
tggagcgaac gacctacacc gaactgagat acctacagcg tgagctatga aaagcgcca    3480 cgcttcccga agggagaaag gcggacaggt atccggtaag cggcagggtc ggaacaggag   3540
agcgcacgag ggagcttcca gggggaaacg cctggtatct ttatagtcct gtcgggtttc   3600
gccacctctg acttgagcgt cgattttttgt gatgctcgtc aggggggcgg agcctatgga   3660
aaaacgccag caacgcggcc ttttttacggt tcctgggctt tgctggcct tttgctcaca    3720 tgcgc                                                                3725

<210> SEQ ID NO 2
<211> LENGTH: 2187
<212> TYPE: DNA
<213> ORGANISM: Artificial Sequence
<220> FEATURE:
<223> OTHER INFORMATION: nucleotide sequence of HGF

<400> SEQUENCE: 2
atgtgggtga ccaaactcct gccagccctg ctgctgcagc atgtcctcct gcatctcctc     60
ctgctcccca tcgccatccc ctatgcagag ggacaaagga aagaagaaa tacaattcat    120 gaattcaaaa atcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgttttgat aaagcaagaa acaatgcct ctggttcccc     300 ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta agagtggcat caaatgtcag ccctggagtt ccatgatacc acacgaacac    480 agcttttttgc cttcgagcta tcggggtaaa gacctacagg aaaactactg tcgaaatcct    540
cgaggggaag aaggggggacc ctggtgtttc acaagcaatc cagaggtacg ctacgaagtc    600
tgtgacattc ctcagtgttc agaagttgaa tgcatgacct gcaatgggga gagttatcga    660
ggtctcatgg atcatacaga atcaggcaag atttgtcagc gctggatca tcagacacca    720 caccggcaca aattcttgcc tgaaagatat cccgacaagg gctttgatga taattattgc    780
cgcaatcccg atggccagcc gaggccatgg tgctatactc ttgaccctca cacccgctgg    840
gagtactgtg caattaaaac atgcgctgac aatactatga atgacactga tgttcctttg    900
gaaacaactg aatgcatcca aggtcaagga gaaggctaca ggggcactgt caataccatt    960
tggaatggaa ttccatgtca gcgttgggat tctcagtatc ctcacgagca tgacatgact   1020
cctgaaaatt tcaagtgcaa ggacctacga gaaaattact gccgaaatcc agatgggtct   1080
gaatcaccct ggtgttttac cactgatcca aacatccgag ttggctactg ctcccaaatt   1140
ccaaactgtg atatgtcaca tggacaagat tgttatcgtg gaatggcaa aaattatatg   1200 ggcaacttat cccaaacaag atctggacta acatgttcaa tgtgggacaa gaacatggaa   1260
gacttacatc gtcatatctt ctgggaacca tgatgcaagta agctgaatga gaattactgc   1320
cgaaatccag atgatgatgc tcatggaccc tggtgctaca cggaaatcc actcattcct   1380 tgggattatt gccctatttc tcgttgtgaa ggtgatacca cacctacaat agtcaattta   1440
gaccatcccg taatatcttg tgccaaaacg aaacaattgc gagttgtaaa tgggattcca   1500
acacgaacaa acataggatg gatggttagt ttgagataca gaaataaaca tatctgcgga   1560
```

-continued

```
ggatcattga taaaggagag ttgggttctt actgcacgac agtgtttccc ttctcgagac    1620
ttgaaagatt atgaagcttg gcttggaatt catgatgtcc acggaagagg agatgagaaa    1680
tgcaaacagg ttctcaatgt tcccagctg  gtatatggcc ctgaaggatc agatctggtt    1740
ttaatgaagc ttgccaggcc tgctgtcctg gatgattttg ttagtacgat tgatttacct    1800
aattatggat gcacaattcc tgaaaagacc agttgcagtg tttatggctg ggctacact     1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtgcccact  tgtttgtgag    2040
caacataaaa tgagaatggt tcttggtgtc attgttcctg gtcgtggatg tgccattcca    2100
aatcgtcctg gtattttgt  ccgagtagca tattatgcaa aatggataca caaaattatt    2160
ttaacatata aggtaccaca gtcatag                                         2187
```

<210> SEQ ID NO 3
<211> LENGTH: 4679
<212> TYPE: DNA
<213> ORGANISM: Artificial Sequence
<220> FEATURE:
<223> OTHER INFORMATION: nucleotide sequence of HGF-X6

<400> SEQUENCE: 3

```
atgtgggtga ccaaactcct gccagccctg ctgctgcagc atgtcctcct gcatctcctc      60
ctgctcccca tcgccatccc ctatgcagag ggacaaagga aagaagaaa  tacaattcat     120
gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa acaatgcct  ctggttcccc     300
ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
tctatcacta gagtggcat  caaatgtcag ccctggagtt ccatgatacc acacgaacac     480
aggtaagaac agtatgaaga aaagagatga agcctctgtc ttttttacat gttaacagtc     540
tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct  taccttaatg cctcaatttg tagatctcgg     720
tatttgtgga tcccttcctt tctacctgta tttgtcctaa taaattgttg acttattaat     780
tcactacttc ctcacagctt tttttggct  ttacaaatcc actggaaagg tatatgggtg     840
tatcactttg tgtatttcgg tgtgcatgtg tagaggggac aaaaatcctc tctcaaacta     900
taaatattga gtatttgtgt attgaacatt tgctataact actaggtttc ttaaataatc     960
ttaatatata aaatgatata gaaaaaggga aattatagtt cgtattattc atctaagtga    1020
agagattaaa acccagggag taaataaatt gtctaaggac taaggttgta tactatttag    1080
gtgatagata tggggcaacc gtatgggttt tatgattaac aaataaactt ctcaccactc    1140
taccatatca acttttccat aaaagagagc tatagtattc tttgcttaaa taaatttgat    1200
tagtgcatga cttcttgaaa acatataaag caaaagtcac atttgattct atcagaaaag    1260
tgagtaagcc atggcccaaa caaagatgc  attaaaatat tctggaatga tggagctaaa    1320
agtaagaaaa atgactttt  aaaaaagttt actgttagga attgtgaaat tatgctgaat    1380
tttagttgca ttataatttt tgtcagtcat acggtctgac aacctgtctt atttctattt    1440
```

```
cccatatga ggaatgctag ttaagtatgg atattaacta ttactactta gatgcattga      1500
agttgcataa tatggataat acttcactgg ttccctgaaa atgtttagtt agtaataagt      1560
ctcttacact atttgttttg tccaataatt tatattttct gaagacttaa ctctagaata      1620
cactcatgtc aaaatgaaag aatttcattg caaaatattg cttggtacat gacgcatacc      1680
tgtatttgtt ttgtgtcaca acatgaaaaa tgatggttta ttagaagttt cattgggtag      1740
gaaacacatt tgaatggtat ttactaagat actaaaatcc ttggacttca ctctaatttt      1800
agtgccattt agaactcaag gtctcagtaa agtagaaat aaagcctgtt aacaaaacac        1860
aagctgaata ttaaaaatgt aactggattt tcaaagaaat gtttactggt attacctgta      1920
gatgtatatt ctttattatg atcttttgtg taaagtctgg cagacaaatg caatatctaa      1980
ttgttgagtc caatatcaca agcagtacaa agtataaaa aagacttggc cttttctaat        2040
gtgttaaaat actttatgct ggtaataaca ctaagagtag ggcactagaa attttaagtg      2100
aagataatgt gttgcagtta ctgcactcaa tggcttacta ttataaacca aaactgggat      2160
cactaagctc cagtcagtca aaatgatcaa aattattgaa gagaataagc aattctgttc      2220
tttattagga cacagtagat acagactaca aagtggagtg tgcttaataa gaggtagcat      2280
ttgttaagtg tcaattactc tattatccct tggagcttct caaaataacc atataaggtg      2340
taagatgtta aaggttatgg ttacactcag tgcacaggta agctaatagg ctgagagaag      2400
ctaaattact tactggggtc tcacagtaag aaagtgagct gaagtttcag cccagattta      2460
actggattct gggctcttta ttcatgttac ttcatgaatc tgtttctcaa ttgtgcagaa      2520 aaaggggc tatttataag aaaagcaata acaaacaag taatgatctc aaataagtaa          2580
tgcaagaaat agtgagattt caaaatcagt ggcagcgatt tctcagttct gtcctaagtg      2640
gccttgctca atcacctgct atcttttagt ggagctttga aattatgttt cagacaactt      2700
cgattcagtt ctagaatgtt tgactcagca aattcacagg ctcatctttc taacttgatg      2760
gtgaatatgg aaattcagct aaatggatgt taataaaatt caaacgtttt aaggacagat      2820
gaaaatgaca gaattttaag gtaaaatata tgaaggaata taagataaag gattttctga     2880
ccttcagcaa aaacataccc actaattagt aaaattaata ggcaaaaaaa agttgcatgc      2940
tcttatactg taatgattat cattttaaaa ctagctttt gccttcgagc tatcgggta         3000 aagacctaca ggaaaactac tgtcgaaatc ctcgagggga agaagggga ccctggtgtt       3060 tcacaagcaa tccagaggta cgctacgaag tctgtgacat tcctcagtgt tcagaagttg      3120
aatgcatgac ctgcaatggg gagagttatc gaggtctcat ggatcataca gaatcaggca      3180
agatttgtca gcgctgggat catcagacac cacaccggca caaattcttg cctgaaagat      3240
atcccgacaa gggctttgat gataattatt gccgcaatcc cgatggccag ccgaggccat      3300
ggtgctatac tcttgacccct cacacccgct gggagtactg tgcaattaaa acatgcgctg     3360
acaatactat gaatgacact gatgttcctt tggaaacaac tgaatgcatc caaggtcaag      3420
gagaaggcta caggggcact gtcaatacca tttggaatgg aattccatgt cagcgttggg      3480
attctcagta tcctcacgag catgacatga ctcctgaaaa tttcaagtgc aaggacctac      3540
gagaaaatta ctgccgaaat ccagatgggt ctgaatcacc ctggtgtttt accactgatc      3600
caaacatccg agttggctac tgctcccaaa ttccaaactg tgatatgtca catggacaag      3660
attgttatcg tgggaatggc aaaaattata tgggcaactt atcccaaaca agatctggac      3720
taacatgttc aatgtgggac aagaacatgg aagacttaca tcgtcatatc ttctgggaac      3780
```

```
cagatgcaag taagctgaat gagaattact gccgaaatcc agatgatgat gctcatggac    3840
cctggtgcta cacgggaaat ccactcattc cttgggatta ttgccctatt tctcgttgtg    3900
aaggtgatac cacacctaca atagtcaatt tagaccatcc cgtaatatct tgtgccaaaa    3960
cgaaacaatt gcgagttgta aatgggattc caacacgaac aaacatagga tggatggtta    4020
gtttgagata cagaaataaa catatctgcg gaggatcatt gataaaggag agttgggttc    4080
ttactgcacg acagtgtttc ccttctcgag acttgaaaga ttatgaagct tggcttggaa    4140
ttcatgatgt ccacggaaga ggagatgaga aatgcaaaca ggttctcaat gtttcccagc    4200
tggtatatgg ccctgaagga tcagatctgg ttttaatgaa gcttgccagg cctgctgtcc    4260
tggatgattt tgttagtacg attgatttac ctaattatgg atgcacaatt cctgaaaaga    4320
ccagttgcag tgtttatggc tggggctaca ctggattgat caactatgat ggcctattac    4380
gagtggcaca tctctatata atgggaaatg agaaatgcag ccagcatcat cgagggaagg    4440
tgactctgaa tgagtctgaa atatgtgctg gggctgaaaa gattggatca ggaccatgtg    4500 aggggggatta tggtggccca cttgtttgtg agcaacataa aatgagaatg gttcttggtg    4560
tcattgttcc tggtcgtgga tgtgccattc caaatcgtcc tggtattttt gtccgagtag    4620
catattatgc aaaatggata cacaaaatta ttttaacata taaggtacca cagtcatag    4679

<210> SEQ ID NO 4
<211> LENGTH: 3679
<212> TYPE: DNA
<213> ORGANISM: Artificial Sequence
<220> FEATURE:
<223> OTHER INFORMATION: nucleotide sequence of HGF-X7

<400> SEQUENCE: 4
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttgat aaagcaagaa acaatgcct ctggttcccc     300 ttcaatagca tgtcaagtgg agtgaaaaaa gaatttggcc atgaatttga cctctatgaa     360 acaaagact acattagaaa ctgcatcatc ggtaaaggac gcagctacaa gggaacagta     420
tctatcacta agagtggcat caaatgtcag ccctggagtt ccatgatacc acacgaacac     480
aggtaagaac agtatgaaga aaagagatga agcctctgtc tttttacat gttaacagtc     540 tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg     720
tatttgtgga tcctgggtag gaaacacatt tgaatggtat ttactaagat actaaaatcc     780
ttggacttca ctctaatttt agtgccattt agaactcaag gtctcagtaa aagtagaaat     840
aaagcctgtt aacaaaacac aagctgaata ttaaaaatgt aactggattt tcaaagaaat     900
gtttactggt attacctgta gatgtatatt ctttattatg atcttttgtg taagtctgg     960 cagacaaatg caatatctaa ttgttgagtc caatatcaca agcagtacaa agtataaaa    1020 aagacttggc ctttctaat gtgttaaaat acttttatgct ggtaataaca ctaagagtag    1080
ggcactagaa attttaagtg aagataatgt gttgcagtta ctgcactcaa tggcttacta    1140
ttataaacca aaactgggat cactaagctc cagtcagtca aatgatcaa aattattgaa    1200
```

```
gagaataagc aattctgttc tttattagga cacagtagat acagactaca aagtggagtg   1260
tgcttaataa gaggtagcat tgttaagtg tcaattactc tattatccct tggagcttct    1320
caaaataacc atataaggtg taagatgtta aggttatgg ttacactcag tgcacaggta    1380
agctaatagg ctgagagaag ctaaattact tactggggtc tcacagtaag aaagtgagct   1440
gaagtttcag cccagattta actggattct gggctcttta ttcatgttac ttcatgaatc   1500
tgtttctcaa ttgtgcagaa aaagggggc tatttataag aaaagcaata aacaaacaag    1560
taatgatctc aaataagtaa tgcaagaaat agtgagattt caaaatcagt ggcagcgatt   1620
tctcagttct gtcctaagtg gccttgctca atcacctgct atcttttagt ggagctttga   1680
aattatgttt cagacaactt cgattcagtt ctagaatgtt tgactcagca aattcacagg   1740
ctcatctttc taacttgatg gtgaatatgg aaattcagct aaatggatgt taataaaatt   1800
caaacgtttt aaggacagat gaaaatgaca gaattttaag gtaaaatata tgaaggaata   1860
taagataaag gattttcta ccttcagcaa aaacataccc actaattagt aaaattaata    1920
ggcaaaaaaa agttgcatgc tcttatactg taatgattat catttttaaaa ctagctttt   1980 gccttcgagc tatcggggta aagacctaca ggaaaactac tgtcgaaatc ctcgagggga   2040
agaaggggga ccctggtgtt tcacaagcaa tccagaggta cgctacgaag tctgtgacat   2100
tcctcagtgt tcagaagttg aatgcatgac ctgcaatggg gagagttatc gaggtctcat   2160
ggatcataca gaatcaggca agatttgtca gcgctgggat catcagacac cacaccggca   2220
caaattcttg cctgaaagat atcccgacaa gggctttgat gataattatt gccgcaatcc   2280
cgatggccag ccgaggccat ggtgctatac tcttgaccct cacacccgct gggagtactg   2340
tgcaattaaa acatgcgctg acaatactat gaatgacact gatgttcctt tggaaacaac   2400
tgaatgcatc caaggtcaag gagaaggcta caggggcact gtcaatacca tttggaatgg   2460
aattccatgt cagcgttggg attctcagta tcctcacgag catgacatga ctcctgaaaa   2520
tttcaagtgc aaggacctac gagaaaatta ctgccgaaat ccagatgggt ctgaatcacc   2580
ctggtgtttt accactgatc caaacatccg agttggctac tgctcccaaa ttccaaactg   2640
tgatatgtca catggacaag attgttatcg tgggaatggc aaaaattata tgggcaactt   2700
atcccaaaca agatctggac taacatgttc aatgtgggac aagaacatgg aagacttaca   2760
tcgtcatatc ttctgggaac cagatgcaag taagctgaat gagaattact gccgaaatcc   2820
agatgatgat gctcatggac cctggtgcta cacgggaaat ccactcattc cttgggatta   2880
ttgccctatt tctcgttgtg aaggtgatac cacacctaca atagtcaatt tagaccatcc   2940
cgtaatatct tgtgccaaaa cgaaacaatt gcgagttgta aatgggattc caacacgaac   3000
aaacatagga tggatggtta gtttgagata cagaaataaa catatctgcg gaggatcatt   3060
gataaaggag agttgggttc ttactgcacg acagtgtttc ccttctcgag acttgaaaga   3120
ttatgaagct tggcttggaa ttcatgatgt ccacggaaga ggagatgaga aatgcaaaca   3180
ggttctcaat gtttcccagc tggtatatgg ccctgaagga tcagatctgg ttttaatgaa   3240
gcttgccagg cctgctgtcc tggatgattt tgttagtacg attgatttac ctaattatgg   3300
atgcacaatt cctgaaaaga ccagttgcag tgtttatggc tggggctaca ctggattgat   3360
caactatgat ggcctattac gagtggcaca tctctatata tgggaaatg agaaatgcag   3420 ccagcatcat cgagggaagg tgactctgaa tgagtctgaa atatgtgctg ggctgaaaa    3480 gattggatca ggaccatgtg aggggatta tggtggccca cttgtttgtg agcaacataa    3540
```

| aatgagaatg gttcttggtg tcattgttcc tggtcgtgga tgtgccattc caaatcgtcc | 3600 |
| tggtattttt gtccgagtag catattatgc aaaatggata cacaaaatta ttttaacata | 3660 |
| taaggtacca cagtcatag | 3679 |

<210> SEQ ID NO 5
<211> LENGTH: 2729
<212> TYPE: DNA
<213> ORGANISM: Artificial Sequence
<220> FEATURE:
<223> OTHER INFORMATION: nucleotide sequence of HGF-X8

<400> SEQUENCE: 5

| atgtgggtga ccaaactcct gccagccctg ctgctgcagc atgtcctcct gcatctcctc | 60 |
| ctgctcccca tcgccatccc ctatgcagag ggacaaagga aaagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgtttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatc ggtaaaggca gcagctacaa gggaacagta | 420 |
| tctatcacta agagtggcat caaatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tccttatgtt tcagacaact tcgattcagt tctagaatgt ttgactcagc | 780 |
| aaattcacag gctcatcttt ctaacttgat ggtgaatatg gaaattcagc taaatggatg | 840 |
| ttaataaaat tcaaacgttt taaggacaga tgaaaatgac agaatttaa ggtaaaatat | 900 |
| atgaaggaat ataagataaa ggattttct accttcagca aaaacatacc cactaattag | 960 |
| taaaattaat aggcaaaaaa aagttgcatg ctcttatact gtaatgatta tcatttaaa | 1020 |
| actagctttt tgccttcgag ctatcggggt aaagacctac aggaaaacta ctgtcgaaat | 1080 |
| cctcgagggg aagaagggg accctggtgt tcacaagca atccagaggt acgctacgaa | 1140 |
| gtctgtgaca ttcctcagtg ttcagaagtt gaatgcatga cctgcaatgg ggagagttat | 1200 |
| cgaggtctca tggatcatac agaatcaggc aagatttgtc agcgctggga tcatcagaca | 1260 |
| ccacaccggc acaaattctt gcctgaaaga tatcccgaca agggctttga tgataattat | 1320 |
| tgccgcaatc ccgatggcca gccgaggcca tggtgctata ctcttgaccc tcacacccgc | 1380 |
| tgggagtact gtgcaattaa acatgcgct gacaatacta tgaatgacac tgatgttcct | 1440 |
| ttggaaacaa ctgaatgcat ccaaggtcaa ggagaaggct acaggggcac tgtcaatacc | 1500 |
| atttggaatg gaattccatg tcagcgttgg gattctcagt atcctcacga gcatgacatg | 1560 |
| actcctgaaa atttcaagtg caaggaccta cgagaaaatt actgccgaaa tccagatggt | 1620 |
| ctgaatcacc ctggtgtttt accactgatc caaacatccg agttggctac tgctcccaaa | 1680 |
| ttccaaactg tgatatgtca catggacaag attgttatcg tgggaatggc aaaaattata | 1740 |
| tgggcaactt atcccaaaca agatctggac taacatgttc aatgtgggac aagaacatgg | 1800 |
| aagacttaca tcgtcatatc ttctgggaac cagatgcaag taagctgaat gagaattact | 1860 |
| gccgaaatcc agatgatgat gctcatggac cctggtgcta cacgggaaat ccactcattc | 1920 |

```
cttgggatta ttgccctatt tctcgttgtg aaggtgatac cacacctaca atagtcaatt    1980
tagaccatcc cgtaatatct tgtgccaaaa cgaaacaatt gcgagttgta aatgggattc    2040
caacacgaac aaacatagga tggatggtta gtttgagata cagaaataaa catatctgcg    2100
gaggatcatt gataaaggag agttgggttc ttactgcacg acagtgtttc ccttctcgag    2160
acttgaaaga ttatgaagct tggcttggaa ttcatgatgt ccacggaaga ggagatgaga    2220
aatgcaaaca ggttctcaat gtttcccagc tggtatatgg ccctgaagga tcagatctgg    2280 tttaatgaa gcttgccagg cctgctgtcc tggatgattt tgttagtacg attgatttac    2340
ctaattatgg atgcacaatt cctgaaaaga ccagttgcag tgtttatggc tggggctaca    2400
ctggattgat caactatgat ggcctattac gagtggcaca tctctatata tgggaaatg    2460 agaaatgcag ccagcatcat cgagggaagg tgactctgaa tgagtctgaa atatgtgctg    2520
gggctgaaaa gattggatca ggaccatgtg aggggggatta tggtggccca cttgtttgtg    2580
agcaacataa aatgagaatg gttcttggtg tcattgttcc tggtcgtgga tgtgccattc    2640
caaatcgtcc tggtatttttt gtccgagtag catattatgc aaaatggata cacaaaatta    2700
ttttaacata taaggtacca cagtcatag                                        2729

<210> SEQ ID NO 6
<211> LENGTH: 2172
<212> TYPE: DNA
<213> ORGANISM: Artificial Sequence
<220> FEATURE:
<223> OTHER INFORMATION: nucleotide sequence of dHGF(deleted varient of
      HGF)

<400> SEQUENCE: 6
atgtgggtga ccaaactcct gccagccctg ctgctgcagc atgtcctcct gcatctcctc    60
ctgctcccca tcgccatccc ctatgcagag ggacaaagga aagaagaaa tacaattcat    120 gaattcaaaa aatcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgttttttgat aaagcaagaa aacaatgcct ctggttcccc    300
ttcaatagca tgtcaagtgg agtgaaaaaa gaatttggcc atgaatttga cctctatgaa    360
aacaaagact acattagaaa ctgcatcatc ggtaaaggac gcagctacaa gggaacagta    420
tctatcacta gagtggcat caaatgtcag ccctggagtt ccatgatacc acacgaacac    480
agctatcggg gtaaagacct acaggaaaac tactgtcgaa atcctcgagg ggaagaaggg    540
ggaccctggt gtttcacaag caatccagag gtacgctacg aagtctgtga cattcctcag    600
tgttcagaag ttgaatgcat gacctgcaat ggggagagtt atcgaggtct catggatcat    660
acagaatcag gcaagatttg tcagcgctgg gatcatcaga caccacaccg gcacaaattc    720
ttgcctgaaa gatatcccga caagggcttt gatgataatt attgccgcaa tcccgatggc    780
cagccgaggc catggtgcta tactcttgac cctcacaccc gctgggagta ctgtgcaatt    840
aaaacatgcg ctgacaatac tatgaatgac actgatgttc ctttggaaac aactgaatgc    900
atccaaggtc aaggagaagg ctacaggggc actgtcaata ccatttggaa tggaattcca    960
tgtcagcgtt gggattctca gtatcctcac gagcatgaca tgactcctga aaatttcaag    1020
tgcaaggacc tacgagaaaa ttactgccga aatccagatg gtctgaatc accctggtgt    1080 tttaccactg atccaaacat ccgagttggc tactgctccc aaattccaaa ctgtgatatg    1140
tcacatggac aagattgtta tcgtgggaat ggcaaaaatt atatgggcaa cttatcccaa    1200
```

```
acaagatctg gactaacatg ttcaatgtgg gacaagaaca tggaagactt acatcgtcat    1260
atcttctggg aaccagatgc aagtaagctg aatgagaatt actgccgaaa tccagatgat    1320
gatgctcatg gaccctggtg ctacacggga atccactca ttccttggga ttattgccct    1380
atttctcgtt gtgaaggtga taccacacct acaatagtca atttagacca tcccgtaata    1440
tcttgtgcca aaacgaaaca attgcgagtt gtaaatggga ttccaacacg aacaaacata    1500
ggatggatgg ttagtttgag atacagaaat aaacatatct gcggaggatc attgataaag    1560
gagagttggg ttcttactgc acgacagtgt ttcccttctc gagacttgaa agattatgaa    1620
gcttggcttg gaattcatga tgtccacgga agaggagatg agaaatgcaa acaggttctc    1680
aatgtttccc agctggtata tggccctgaa ggatcagatc tggttttaat gaagcttgcc    1740
aggcctgctg tcctggatga ttttgttagt acgattgatt tacctaatta tggatgcaca    1800
attcctgaaa agaccagttg cagtgtttat ggctggggct acactggatt gatcaactat    1860
gatggcctat tacgagtggc acatctctat ataatgggaa atgagaaatg cagccagcat    1920
catcgaggga aggtgactct gaatgagtct gaaatatgtg ctggggctga aaagattgga    1980
tcaggaccat gtgaggggga ttatggtggc ccacttgttt gtgagcaaca taaaatgaga    2040
atggttcttg gtgtcattgt tcctggtcgt ggatgtgcca ttccaaatcg tcctggtatt    2100
tttgtccgag tagcatatta tgcaaaatgg atacacaaaa ttattttaac atataaggta    2160
ccacagtcat ag                                                       2172

<210> SEQ ID NO 7
<211> LENGTH: 477
<212> TYPE: DNA
<213> ORGANISM: Artificial Sequence
<220> FEATURE:
<223> OTHER INFORMATION: nucleotide sequence of IGF-1

<400> SEQUENCE: 7
atgggaaaaa tcagcagtct tccaacccaa ttatttaagt gctgcttttg tgatttcttg     60
aaggtgaaga tgcacaccat gtcctcctcg catctcttct acctggcgct gtgcctgctc    120
accttcacca gctctgccac ggctggaccg agacgctct gcggggctga gctggtggat    180
gctcttcagt tcgtgtgtgg agacaggggc ttttatttca acaagcccac agggtatggc    240
tccagcagtc ggagggcgcc tcagacaggc atcgtggatg agtgctgctt ccggagctgt    300
gatctaagga ggctggagat gtattgcgca cccctcaagc ctgccaagtc agctcgctct    360
gtccgtgccc agcgccacac cgacatgccc aagacccaga gtatcagcc ccatctacc    420 aacaagaaca cgaagtctca gagaaggaaa ggaagtacat ttgaagaacg caagtag     477

<210> SEQ ID NO 8
<211> LENGTH: 576
<212> TYPE: DNA
<213> ORGANISM: Artificial Sequence
<220> FEATURE:
<223> OTHER INFORMATION: nucleotide sequence of VEGF

<400> SEQUENCE: 8
atgaactttc tgctgtcttg ggtgcattgg agccttgcct tgctgctcta cctccaccat     60
gccaagtggt cccaggctgc acccatggca gaaggaggag ggcagaatca tcacgaagtg    120
gtgaagttca tggatgtcta tcagcgcagc tactgccatc caatcgagac cctggtggac    180
atcttccagg agtaccctga tgagatcgag tacatcttca agccatcctg tgtgcccctg    240
```

```
atgcgatgcg ggggctgctg caatgacgag ggcctggagt gtgtgcccac tgaggagtcc      300
aacatcacca tgcagattat gcggatcaaa cctcaccaag ccagcacat aggagagatg       360 agcttcctac agcacaacaa atgtgaatgc agaccaaaga aagatagagc aagacaagaa      420
aatccctgtg ggccttgctc agagcggaga aagcatttgt ttgtacaaga tccgcagacg      480
tgtaaatgtt cctgcaaaaa cacagactcg cgttgcaagg cgaggcagct tgagttaaac     540
gaacgtactt gcagatgtga caagccgagg cggtga                                576

<210> SEQ ID NO 9
<211> LENGTH: 468
<212> TYPE: DNA
<213> ORGANISM: Artificial Sequence
<220> FEATURE:
<223> OTHER INFORMATION: nucleotide sequence of FGF-1

<400> SEQUENCE: 9
atggctgaag agaaaatcac caccttcaca gccctgacag aaaagtttaa cctgcctcca      60
gggaactaca agaagcccaa actcctctac tgtagcaatg gaggccactt cctgaggatc     120
cttcctgatg gcactgtgga tgggaccagg acaggtctg accagcacat tcagctgcag      180
ctcagtgctg aatcagtggg agaggtgtac attaagagta cagagactgg ccagtacttg     240
gccatggaca ctgatggact tctgtatggc tcacagacac aaatgagga atgcttgttc      300 ctggaaaggc tggaggagaa ccattacaac acctatatct ccaagaagca tgcagagaag    360
aattggtttg ttggcctcaa gaagaatggg agctgcaaaa gaggtcctag aactcactat     420
ggccagaaag ccatcttgtt tctccccctg ccagtctctt ctgactaa                  468

<210> SEQ ID NO 10
<211> LENGTH: 621
<212> TYPE: DNA
<213> ORGANISM: Artificial Sequence
<220> FEATURE:
<223> OTHER INFORMATION: nucleotide sequence of FGF-4

<400> SEQUENCE: 10
atgtcggggc ccgggacggc cgcggtagcg ctgctcccgg cggtcctgct ggccttgctg       60
gcgccctggg cgggccgagg gggcgccgcc gcacccactg cacccaacgg cacgctggag     120
gccgagctgg agcgccgctg ggagagcctg gtggcgctct cgttggcgcg cctgccggtg     180
gcagcgcagc ccaaggaggc ggccgtccag agcggcgccg gcgactacct gctgggcatc     240
aagcggctgc ggcggctcta ctgcaacgtg ggcatcggct ccacctcca ggcgctcccc      300 gacggccgca tcggcggcgc gcacgcggac acccgcgaca gctgctgga gctctcgccc     360 gtggagcggg gcgtggtgag catcttcggc gtggccagcc ggttcttcgt ggccatgagc     420
agcaagggca agctctatgg ctcgcccttc ttcaccgatg agtgcacgtt caaggagatt     480
ctccttccca caactacaa cgcctacgag tcctacaagt accccggcat gttcatcgcc      540
ctgagcaaga atgggaagac caagaagggg aaccgagtgt cgcccaccat gaaggtcacc     600
cacttcctcc ccaggctgtg a                                                621

<210> SEQ ID NO 11
<211> LENGTH: 726
<212> TYPE: DNA
<213> ORGANISM: Artificial Sequence
<220> FEATURE:
<223> OTHER INFORMATION: nucleotide sequence of PDGF B

<400> SEQUENCE: 11
```

```
atgaatcgct gctgggcgct cttcctgtct ctctgctgct acctgcgtct ggtcagcgcc      60
gagggggacc ccattcccga ggagctttat gagatgctga gtgaccactc gatccgctcc     120
tttgatgatc tccaacgcct gctgcacgga gaccccggag aggaagatgg ggccgagttg     180
gacctgaaca tgacccgctc ccactctgga ggcgagctgg agagcttggc tcgtggaaga     240
aggagcctgg gttccctgac cattgctgag ccggccatga tcgccgagtg caagacgcgc     300
accgaggtgt tcgagatctc ccggcgcctc atagaccgca ccaacgccaa cttcctggtg     360
tggccgccct gtgtggaggt gcagcgctgc tccggctgct gcaacaaccg caacgtgcag     420
tgccgcccca cccaggtgca gctgcgacct gtccaggtga gaaagatcga gattgtgcgg     480
aagaagccaa tctttaagaa ggccacggtg acgctggaag accacctggc atgcaagtgt     540
gagacagtgg cagctgcacg gcctgtgacc cgaagcccgg ggggttccca ggagcagcga     600
gccaaaacgc cccaaactcg ggtgaccatt cggacggtgc gagtccgccg gcccccaag     660 ggcaagcacc ggaaattcaa gcacacgcat gacaagacgg cactgaagga gacccttgga     720
gcctag                                                                726
```